US012806076B2

(12) United States Patent
Homer

(10) Patent No.: US 12,806,076 B2
(45) Date of Patent: Nov. 24, 2026

(54) MICROBUBBLE DETECTION

(71) Applicant: Stroma Medical Corporation, Irvine, CA (US)

(72) Inventor: Gregg Homer, Irvine, CA (US)

(73) Assignee: STROMA MEDICAL CORPORATION, Irvine, CA (US)

( * ) Notice: Subject to any disclaimer, the term of this patent is extended or adjusted under 35 U.S.C. 154(b) by 199 days.

(21) Appl. No.: 18/664,171

(22) Filed: May 14, 2024

(65) Prior Publication Data

US 2025/0352394 A1 Nov. 20, 2025

(51) Int. Cl.
*A61F 9/008* (2006.01)

(52) U.S. Cl.
CPC *A61F 9/00814* (2013.01); *A61F 2009/00863* (2013.01)

(58) Field of Classification Search
None
See application file for complete search history.

(56) References Cited

U.S. PATENT DOCUMENTS

| | | | | |
|---|---|---|---|---|
| 11,278,452 | B1 * | 3/2022 | Homer | A61F 9/008 |
| 11,547,606 | B2 * | 1/2023 | Margalit | A61F 9/00825 |
| 2006/0106371 | A1 * | 5/2006 | Muhlhoff | A61F 9/00804 606/5 |
| 2006/0111697 | A1 * | 5/2006 | Brinkmann | A61B 18/20 606/4 |
| 2023/0029661 | A1 * | 2/2023 | Benson | A61F 9/008 |

* cited by examiner

*Primary Examiner* — Michael W Kahelin
(74) *Attorney, Agent, or Firm* — Foley & Lardner LLP

(57) ABSTRACT

Methods and systems described herein determine the power to apply to an eye to change the color without damaging the eye. For example, the system may apply, using a first laser supply, a treatment beam to an eye to cause a treatment effect, such as formation of microbubbles. The system may apply, using a second laser supply, a probe beam to the eye to create a backscatter pattern based on detected microbubbles resulting from the treatment effect. The system may determine the backscatter pattern using a backscatter detector and determine the treatment effect based on the backscatter pattern. The system may modulate a power of the first laser supply based on the treatment effect.

42 Claims, 8 Drawing Sheets

200

MICROBUBBLE DETECTION

BACKGROUND

The use of lasers for eye surgery has increased recently. However, while laser eye surgery is a known option for the correction of one or more vision problems, such as nearsightedness (myopia), farsightedness (hyperopia), astigmatism, presbyopia, and cataracts, far less interest has been shown in operations other than those for correcting vision problems. As a result, recent advancements in laser eye surgeries have focused on operations through which a laser may reshape a patient's cornea or replaced a patient's crystalline lens and have generally ignored other parts of a patient's eye and procedures therefor.

SUMMARY

In view of this, methods and systems are discussed herein for delivering laser light to an eye of a patient. In particular, the methods and systems discussed herein determine how much power to apply to an eye to achieve an effect without damaging the eye. The methods and systems must overcome several technical hurdles. For example, in conventional laser eye surgeries (e.g., those aiming to correct vision), the amount of laser power utilized may be somewhat arbitrary and/or variable. If such systems were applied to the pigmented target iris, retina, trabecular meshwork (TM), or iris pigment epithelium (IPE), this may lead to inconsistent results and potential damage to the target tissue. In view of these technical hurdles, the methods and systems discussed herein deliver laser light to pigmented target tissues at a laser power relative to a power at which microbubbles are detected in the target tissue, wherein the microbubbles form as a result of the power of the laser light delivered to the target tissue. The system may then deliver a treatment laser at a fraction or a multiple of this power, based on the intended goal of the session (e.g., to denature pigment in the eye, to ablate pigment in the eye, to physically injure pigment cells without rupturing them, or to achieve another goal). Moreover, eye procedures may be performed over several sessions, and the eye may be different at each session. Thus, the correct power level may be different for each session. The microbubbles may indicate, at any given session, a power level at which the system may safely and effectively deliver laser light to the eye.

The methods and systems discussed herein may be used for many purposes, both cosmetic and therapeutic. Many ophthalmic procedures rely on pigment as a chromophore for laser energy. The absorption coefficient of the pigment may determine a minimum power required to achieve efficacy and a maximum power to mitigate the risk of injury. Pigment may serve as a chromophore in the iris, retina, TM, and IPE of the eye. Examples of procedures that rely upon pigment as a chromophore for laser energy include laser peripheral iridoplasty; selective laser trabeculoplasty (SLT); argon laser trabeculoplasty (ALT); retinal photocoagulation (e.g., for the treatment of retinal holes or tears, retinal detachment, diabetic retinopathy, macular edema, age-related macular degeneration, and retinal vein occlusion); therapeutic iris iridoplasty (e.g., for the treatment of glaucoma); and aesthetic iris iridoplasty (e.g., laser eye color change). Systems and methods for therapeutic iris iridoplasty are disclosed in U.S. patent Ser. No. 13/456,111, which is hereby incorporated by reference in its entirety. Systems and methods for aesthetic iris iridoplasty are disclosed in U.S. Pat. Nos. 11,160,685, 11,160,685, and U.S.

application Ser. No. 18/487,889, which are hereby incorporated by reference in their entirety.

These methods and systems provide numerous advantages over conventional methods. For example, in the case of laser peripheral iridoplasty, SLT, ALT, retinal photocoagulation, therapeutic iris iridoplasty, and aesthetic iris iridoplasty, too much laser power applied to the target pigmented tissue (i.e., the iris, TM, retina), can induce unwanted injuries in the target tissue, as well as other non-targeted pigmented tissues to which the laser power might accidentally be applied (e.g., the retina in the cases of therapeutic iris iridoplasty and aesthetic iris iridoplasty). The methods and systems overcome the shortcomings of conventional systems by identifying and delivering an effective laser power to the target pigmented tissue based on detected microbubbles, without inducing unwanted injuries in target or non-target pigmented tissue. Such delivery has advantages in that the settings of the laser system are directed to an outcome rather than sent to arbitrary parameters that may or may not result in damage to the eye.

However, despite the advantages of delivering laser power based on detected microbubbles, such delivery must overcome a fundamental technical issue. Namely, the laser system must be able to detect and/or measure the microbubbles in a safe, non-invasive, and/or precise manner. Moreover, the detection and/or measurement of the microbubbles must not affect the ongoing laser procedure. To overcome this fundamental, technical hurdle, the methods and systems detect and/or measure the microbubbles using a backscatter pattern. A backscatter pattern refers to the scattering of waves or particles in the backward direction, opposite to the direction of the incident wave or particle. To detect this backscatter pattern, the methods and systems may use a secondary beam (e.g., a probe beam) delivered in parallel to or on-axis with the treatment beam. The probe beam, which does not affect treatment, creates a backscatter pattern based on the microbubbles resulting from the treatment effect.

In some aspects, methods and systems for identifying and delivering an effective laser power to the target pigmented tissue may include applying dual beams to the eye to cause a treatment effect in the eye and to detect the treatment effect. The methods and systems can then determine a laser power level based on the detected treatment effect. For example, the treatment effect may be a microbubble formation. In some embodiments, the treatment effect may be a small microbubble formation as opposed to a larger formation (e.g., champagne bubbles). The system may require a high enough power output to achieve the desired pigment effect, but a low enough power output such that the laser does not cause unwanted damage to the eye. In some embodiments, the system may select an initial power output of the first laser supply and may increase the power output until reaching the proper power output. For example, the system may determine the proper power output based on detecting microbubbles in the eye using a probe beam. The system may apply the probe beam to the eye using a second laser supply. In some embodiments, the probe beam may detect the treatment effect in the eye. Applying the probe beam to the eye may create a backscatter based on the microbubbles resulting from the treatment effect. In some embodiments, the system may measure the size and time dependence of the power of the backscatter as monitored at a single localized point (e.g., a treatment beam spot, as detected on a single-element photodiode). In some embodiments, the system may measure a special backscatter pattern as monitored at several locations. The system may detect the backscatter using a backscatter detector and may determine the treatment effect based on the backscatter. Finally, the system may modulate a power of the first laser supply based on detecting the treatment effect. For example, the system may adjust the power output of the first laser supply based on microbubble formations detected in the eye. Thus, the system may determine, based on detected microbubbles, the proper power output of a treatment beam for changing eye color without damaging the eye.

Various other aspects, features, and advantages of the invention will be apparent through the detailed description of the invention and the drawings attached hereto. It is also to be understood that both the foregoing general description and the following detailed description are examples and not restrictive of the scope of the invention. As used in the specification and in the claims, the singular forms of "a," "an," and "the" include plural referents unless the context clearly dictates otherwise. In addition, as used in the specification and the claims, the term "or" means "and/or" unless the context clearly dictates otherwise. Additionally, as used in the specification "a portion," refers to a part of, or the entirety of (i.e., the entire portion), a given item (e.g., data) unless the context clearly dictates otherwise.

DETAILED DESCRIPTION

In the following description, for the purposes of explanation, numerous specific details are set forth in order to provide a thorough understanding of the embodiments of the invention. It will be appreciated, however, by those having skill in the art, that the embodiments of the invention may be practiced without these specific details or with an equivalent arrangement. In other cases, well-known structures and devices are shown in block diagram form in order to avoid unnecessarily obscuring the embodiments of the invention.

The present disclosure provides improved methods and systems for facilitating medical procedures to change eye color and/or perform other procedures related to the eye. Such medical procedures may involve delivering laser power to portions of the eye such that a biological reaction occurs that alters the pigment structure of the eye and thereby changes its color or instigates other desired effects. Determining the proper laser power to use based on the needs of the procedure, safety to the patient, variations from patient to patient, and variations from treatment to treatment (for a multistage treatment) may be critical to a successful outcome. Thus, the methods and systems described herein facilitate determining the proper laser power based on detecting microbubbles forming in the eye.

Exemplary Procedure: Iris Color Alteration

Figure 1:
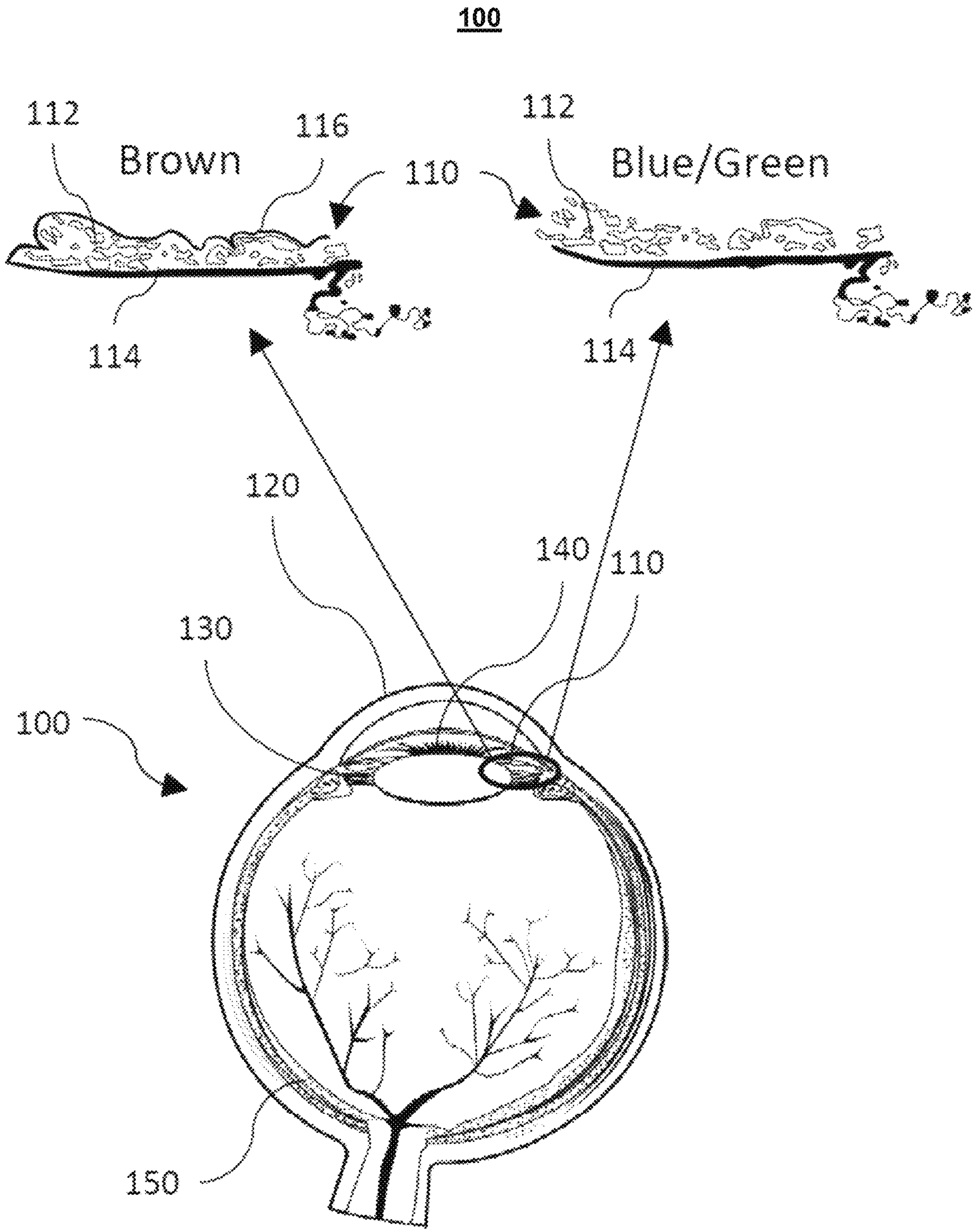
FIG. 1 shows a simplified diagram of the eye and iris, in accordance with one or more embodiments.

Exemplary embodiments of the present disclosure are applicable to the iris color alteration procedure. Before describing this procedure, a brief overview of the anatomy of the eye is provided. As shown in FIG. 1, eye 100 is composed of several anatomical structures, a few of which are discussed below. Central to the present disclosure, the iris 110 is responsible for the color of the eye. Other portions of the eye include, for example, cornea 120, lens 130, pupil 140, and retina 150. While care should be taken to avoid damaging any part of the eye, in the practice of laser safety, special precautions should be taken to avoid directing unwanted laser light through the pupil and into the lens as this part of the eye naturally focuses light onto the retina. Such focusing of already intense laser light may result in injury to the retinal nerves.

Shown in the insets above the eye are two examples of irises. The example on the left is a depiction of an iris 110 in a person with brown eyes. The example on the right depicts an iris 110 of a person with blue or green eyes. The perceived color is due to light reaching the eye being separated into its component wavelengths by stromal fibers in the middle region of the iris—referred to as the iris stroma 112. The separation is similar to the separation exhibited when light passes through a prism. In both cases, the iris has a posterior surface 114 that contains a fairly thick (several cells deep) layer of pigmentation that primarily absorbs visible light wavelengths longer than blue or green. However, in the example on the left for a person with brown eyes, there is an additional anterior surface that contains brown pigment (e.g., stromal pigment 116). The brown stromal pigment gives the eye a brown color. Eyes without the stromal pigment reflect mostly blue or green light, as described above, giving the eye a blue or green color.

A brief summary of an iris color alteration procedure as referenced herein is provided. Laser light may be delivered to reduce the density of the anterior iris pigment. This process may make the eye appear a lighter brown or a deeper blue/green.

Included in the present disclosure are methods for the improved delivery of laser light for performing the above-described iris color alteration procedure. One way to deliver a consistent and clinically safe amount of laser light that is still effective for performing the iris color alteration procedure may include the system determining laser criteria in terms of this safe amount based on detecting microbubbles forming in the eye.

The laser settings used for the iris color alteration procedure, as described in the present disclosure, may be determined by the system based on the minimum required radiative exposure (MRE) at the iris plane of the eye.

The MRE is the minimum radiative exposure value capable of denaturing the pigment granules (melanosomes) within the pigment cells (melanocytes) located primarily over the anterior surface of the iris of the eye and secondarily and at lesser density within the stromal fibers of the iris of the eye. Denaturation of these pigment granules occurs at or about the temperature at which microbubbles first occur on the surfaces of the granules. These microbubbles typically occur at approximately 120° C. These microbubbles need not be maintained for a long duration or recreated multiple times. A single exposure may be sufficient to induce denaturation of the granule. Once a critical mass of these granules is denatured within a given cell, the cell will die off, signaling macrophages residing in and about the iris to digest the cell and remove it through the vasculature of the iris.

The descriptions of exemplary laser powers that may be delivered are used to cause biological actions that result in the desired alteration in eye color. Accordingly, various methods of calibrating a delivered dose may be used, such as monitoring temperature (e.g., using a temperature sensor) or monitoring an effect of the dose (e.g., microbubble formation). In some implementations, the laser power may be sufficient to cause a concurrent temperature change in the stroma pigment, which then causes macrophages in the iris to remove at least a portion of the stromal pigment. In this way, monitoring of the iris temperature may be performed by the system to determine the MRE (e.g., detecting the exposure at which microbubbles begin to form). To facilitate delivery of laser power to cause sufficient temperature changes in the stromal pigment, some methods may include determining, with a temperature sensor, a temperature of at least a portion of the iris that contains stromal pigment. In some embodiments, the temperature sensor may be of a type that is non-invasive to the iris. Examples of temperature sensors may include more direct temperature sensors such as passive infrared detectors that image the eye or more indirect temperature sensors utilizing acoustical monitoring that detects acoustical signals (sounds or pressure waves) indicative of microbubble formation (e.g., as expected to occur around a pre-determined temperature and thus an approximation of the temperature crossing that threshold). Heat transfer from within the iris may manifest itself as local heating at the surface of the eye. Computer modeling of predicted or a priori heat patterns may be associated with the measured heat pattern to derive a heat pattern at the activated stromal pigment. For example, with an implementation that utilizes an infrared imaging system, the received infrared radiation may be converted by the imaging system, or a connected computer receiving data from such, to a local temperature in the iris. Such a conversion may be performed using a blackbody approximation or other similar methods.

One factor complicating ascertainment of the MRE is that it may vary from one melanosome to the next based upon the absorption coefficient between the wavelength of the radiative energy and the color value and/or density of the melanosome. If the MRE is too low for a given melanosome, no microbubbles will form, the melanosome will not be denatured, and its melanocyte will not be digested and eliminated. Conversely, if the MRE is too high for a given melanosome, too much heat will be generated within the melanocyte, ablating the melanocytes and causing them to burst, releasing the melanosomes into the anterior chamber of the eye, potentially causing inflammation in the adjacent tissues and its associated adverse conditions. The MRE for a given melanosome must therefore be appropriate for each melanosome. In some embodiments, denaturation may occur at the melanocyte level or at the melanosome level.

By way of example, a 532 nm wavelength may be generated by the laser system to treat an iris with melanosomes having three color values/densities: tan, medium brown, and dark brown. The MRE required to denature the dark brown melanosomes will be lower than the MRE required to denature the tan and medium brown melanosomes (because the absorption coefficient between the wavelength and the dark brown color value/density is higher). The MRE required to denature the medium brown melanosomes will be higher than the MRE required to denature the dark brown melanosomes (because the absorption coefficient between the wavelength and the medium brown color value/density is lower), and the MRE required to denature the medium brown melanosomes will be lower than the MRE required to treat the tan melanosomes (because the absorption coefficient between the wavelength and the medium brown color value/density is higher). And the MRE required to denature the tan melanosomes will be higher than the MRE required to denature the medium and dark brown melanosomes (because the absorption coefficient between the wavelength and the tan color value/density is lower). Denaturation of the stromal melanosomes of this iris will therefore require three different MREs.

Real-time detection of the melanosome surface microbubbles will inform each MRE in the above example. In one embodiment, the initial radiant exposure value is too low to induce microbubbles but is gradually increased until microbubbles are first detected. An initial MRE, “MRE I,” may be a fraction or multiple of the microbubble fluence. The entire iris may then be treated using MRE I. This treatment will denature the dark brown melanosomes, and their melanocytes will be digested and eliminated over the next 3-4 weeks. At 4 weeks, the treatment protocol may be repeated. Because most or all of the dark brown melanosomes are eliminated, the first microbubbles will be detected at a higher radiant exposure value. Let us call this “MRE II.” The entire iris may then be treated using MRE II. This treatment will denature the medium brown melanosomes, and their melanocytes will be digested and eliminated over the next 3-4 weeks. At 4 weeks, the treatment protocol may be repeated. Because most or all of the medium brown melanosomes are eliminated, the first microbubbles will be detected at a higher radiant exposure value. Let us call this “MRE III.” The entire iris may then be treated using MRE III. This treatment will denature the tan melanosomes, and their melanocytes will be digested and eliminated over the next 3-4 weeks. If stromal melanocytes remain on the anterior iris surface, treatment may be repeated using MRE III.

If melanocytes remain within the iris stroma, they will absorb the backscattered blue or green light, making the gray of the stroma fibers more visible, producing a gray-blue or gray-green perceived iris color. Many patients are satisfied with this perceived color because the gray increases the color value of the eye, making them appear brighter. For those patients who prefer a more saturated blue or green color hue, the treatment may be repeated at the MRE III value but with the laser beam waist shifted from the anterior iris surface to the interior stroma. This treatment will denature the melanocytes remaining within the iris stroma and eliminate or reduce the absorption of the backscattered blue or green light.

In one implementation, the following exemplary MRE ranges are given for each of the following melanosome color values/densities, where $\lambda$=532 nm, t=11.475 ns, the pulse repetition rate (prr)=135 kHz, and the incidence angle of the beam to the iris plane ($\theta_i$)=0°:

| MRE | Color Value/Density | MRE Range (mJ/cm$^2$) |
|---|---|---|
| MRE I | Dark brown | 250-400 |
| MRE II | Medium brown | 550-650 |
| MRE III | Tan | 750-850 |

The above MRE ranges are specific to the laser radiation parameters described above, but may vary with changes in these parameters. The elimination of the stromal pigment is preferably performed by initiation of macrophagic digestion of the stromal pigment. However, in some implementations, the elimination may be caused by ablation of the stromal pigment. Typically, ablation is caused by higher laser powers than those used to initiate macrophagic digestion. In some embodiments, ablation may involve tissue removal from the body. For example, ablation may include the removal of solid material by directly driving it to gaseous or plasma state by high-fluence laser pulses. In some embodiments, ablation may mean lysing, rupturing, destruction, or elimination.

Laser Criteria

Laser criteria may include any settings for the laser system such as energy per pulse, spot size, pulse duration, pulse width, repetition rate, beam profile, beam angle, beam position, etc. Accordingly, it is contemplated that there may be multiple sets of such laser criteria that satisfy the restriction on the exposure described above.

In some implementations, the difference given above may be due to the convergence and divergence angle(s) of the beam (i.e., a larger angle produces a lower power density anterior and posterior to the focal point of the beam). Various implementations may include generation of a Gaussian beam that may be converging anterior (in front of) to the iris with at least a portion diverging posterior (behind) the iris. The focal plane (i.e., the location of the beam waist) may therefore be anywhere in this range, such as being within the iris itself, but optionally further in front of the iris. When the present disclosure refers to focusing laser power at the target tissue, this means that the laser power may be focused on a specific location, which may include, the anterior or posterior surface of the iris or fundus or a particular cell layer in the iris, fundus, or specific layer therein.

The convergence and divergence of the beam and the size and location of the beam waist set the spot size at the target. For example, if the beam waist is at the target, the spot size is the beam waist. However, if the beam waist is in front or behind the target, the spot size will be larger based on the convergence or divergence of the beam. Because a spot size does not have sharp edges, the measurement must be defined by a specific measurement convention. Exemplary conventions comprise FWHM, 1/e, $1/e^2$, D4σ, 10/90 or 20/80 knife-edge, and D86. Unless otherwise indicated herein, spot size shall refer to spot width, as defined by the $1/e^2$ convention. Some methods may include determining a spot size for laser light to be delivered to a target tissue surface. The determination may include retrieving a set of laser criteria that result in delivery of laser light having a spot size of, for example, 4-70 microns, inclusive, to the target tissue. In some embodiments, laser light having a spot size of, for example, 80 to 500 microns, inclusive, may be delivered. In some embodiments, laser light having a different spot size may be delivered. From the available set of laser criteria, a particular laser criterion may be selected to control the laser system to generate a laser having a desired spot size. The laser system may be set to deliver the laser light at the spot size and then to deliver the laser light. In some embodiments, the system may determine that spot size may be between 4-50, 10-60, 20-30, 25-30, 20-60, 80-120, 250-350, 350-500, or 30-60 microns, or the spot size may fall within a different range. Such spot sizes may be created utilizing at least one positive lens. Thus, the present disclosure contemplates that the spot size, in combination with the laser power, may be selected to be sufficient to cause a power density and concurrent temperature change (and/or possible acoustic effect) in the target tissue, thereby causing initiation of macrophagic digestion of the pigment while being safe for the patient. In some implementations, the spot size of the laser system may be set (and largely constant) with the laser power being adjusted as described herein.

The depth of focus of the laser beam (DOF) may be defined as that portion of the beam axis where the fluence of the beam is at least 80-90% of the fluence at the beam waist, i.e., where S=110.8-0.9. Using 90% this and the other laser parameters from the disclosed example, Equation (7) gives z=0.707412185 mm, and DOF=1.41462437 mm.

This relatively short DOF demands reasonably high-resolution range-finding to identify the location of the initial focal plane and place the beam waist at the desired location in relation to the initial focal plane, as well as reasonably high-resolution auto-focusing to maintain the desired location of the beam waist relative to the focal plane. These high-resolution systems are discussed herein. In one implementation, the beam waist may be located within the pigment layer or slightly anterior to the anterior iris surface.

A laser may include any device capable of generating a beam of optical radiation, whether in the infrared, visible light, or ultraviolet light spectrum. The term "laser" is not intended to restrict (a) the properties of the optical radiation in terms of monochromaticity or coherence (e.g., divergence or directionality); (b) whether the radiation is continuous or pulsed; (c) if pulsed, the specific pulse width (e.g., zeptosecond, attosecond, femtosecond, picosecond, nanosecond, millisecond, or microsecond); (d) the repetition rate; (e) the laser power; (f) the wavelength or frequency of the beam; (g) the number of wavelengths or frequencies, i.e., single v. multi-frequency output (e.g., intense pulsed light); (h) the number of beams, i.e., single v. multiple beams (e.g., splitting of a single beam or generating multiple beams from multiple lasers); or (i) the gain medium.

As used herein, when referring to reducing, lowering, lessening, etc., in the context of adjusting the laser power, this is understood to mean that the laser system may reduce the laser power from a current value to a lower (nonzero) value while still delivering laser light in some respect. These definitions also include redirecting a portion of the laser beam (e.g., to a beam dump) such that the delivered laser power is reduced. These definitions also include attenuating the beam power (e.g., with a Pockels cell or an electro- or acousto-optical modulator) or turning off the laser system (i.e., lowering the laser power to zero). Lastly, reducing the laser power may also include performing any of the above in a repetitive fashion, thereby lowering the duty cycle of the laser beam or performing any combination of the above in an intermittent fashion.

As used herein, when referring to increasing, raising, adding, etc., in the context of adjusting the laser power, this is understood to mean that the laser system may increase the laser power from a current value to a higher value. These definitions also include turning on the laser system. Lastly, increasing the laser power may also include performing any of the above in a repetitive fashion, thereby increasing the duty cycle of the laser beam or performing any combination of the above in an intermittent fashion.

In some aspects, methods and systems for altering pigmented tissue (e.g., a patient's eye color) may include applying dual beams to the eye to cause a treatment effect in the eye and to detect the treatment effect. The methods and systems can then determine a laser power level based on the detected treatment effect. In particular, the system may apply a treatment beam to an eye to cause a treatment effect. For example, the treatment effect may be a microbubble formation. The system may require a high enough power output to change the eye color, but a low enough power output such that the laser does not damage the eye. In some embodiments, the system may select an initial power output of the first laser supply and may increase the power output until reaching the proper power output. For example, the system may determine the proper power output based on detecting microbubbles in the eye using a probe beam. The system may apply the probe beam to the eye using a second laser supply. In some embodiments, the probe beam may detect the treatment effect in the eye. Applying the probe beam to the eye may create a backscatter pattern based on the microbubbles resulting from the treatment effect. The system may determine the backscatter pattern using a backscatter detector and may determine the treatment effect based on the backscatter pattern. Finally, the system may modulate a power of the first laser supply based on detecting the treatment effect. For example, the system may adjust the power output of the first laser supply based on microbubble formations detected in the eye. Thus, the system may determine, based on detected microbubbles, the proper power output of a treatment beam for changing eye color without damaging the eye.

In some embodiments, a backscatter pattern may refer to the scattering of waves or particles in the backward direction, opposite to the direction of the incident wave or particle. This may occur when waves or particles encounter obstacles or surfaces that reflect or scatter them back toward the source. Backscatter patterns may be observed and analyzed using various systems. For example, in radar systems, backscatter patterns are used to analyze the reflections of radar signals from targets. The information obtained helps in detecting and identifying objects. Similar principles apply to underwater or medical imaging that uses acoustic waves. The backscatter patterns can provide insights into the composition and structure of the medium through which the waves travel. In X-ray imaging, backscatter patterns are relevant when X-rays encounter different materials. The amount and pattern of backscattered X-rays can be analyzed to gain information about the material properties.

In some embodiments, methods and systems for this procedure may use multiple beams to generate and detect microbubbles in the eye. In some embodiments, a beam may be a narrow, focused light emitted by a laser supply. This light may be coherent or monochromatic, or the light may possess other qualities. Coherence may refer to a fixed relationship between the phase of waves in a beam of radiation of a single frequency. This coherence may allow the beam to remain narrow over great distances, unlike ordinary light, which spreads out. A monochromatic beam may be composed of a narrow range of output wavelengths, resulting in a pure color. In some embodiments, a beam may be highly collimated, meaning the light rays may be parallel and spread minimally as they travel. In some embodiments, a beam may be any radiation pathway, including light or any other form of electromagnetic radiation. In some embodiments, to safely perform an eye-color change procedure, the system may use multiple beams, such as a treatment beam to cause a treatment effect and a probe beam to measure the treatment effect.

A collimated beam may refer to a set of light rays or other waves that are parallel and have a consistent direction. In a collimated beam, the rays remain parallel and do not converge or diverge over a certain distance. This characteristic is achieved by passing the light or waves through a collimator. All the rays in a collimated beam are parallel to each other. This means that if you extend the rays backward or forward, they will not converge or diverge significantly. The direction of the rays remains the same throughout the beam. There is minimal spreading of the beam over distance. In some embodiments, the collimation process may be achieved using lenses, mirrors, or other optical elements that correct and align the incoming waves or rays.

The system may include a first laser supply that emits a treatment beam. A laser supply may provide electrical energy necessary to operate a laser. A power supply may convert electrical energy from an external source into a form that is suitable for energizing a gain medium, which in turn generates laser light. A gain medium may be a material responsible for the amplification of light through the process of stimulated emission. The gain medium may be in various states of matter, such as solid, liquid, or gas, or a semiconductor. In some embodiments, a gain medium of the first laser supply may be Nd:YAG. In some embodiments, a gain medium of the first laser supply may be Nd:YLF. In some embodiments, a gain medium of the first laser supply may be semiconductor materials layered to form a diode. In some embodiments, a gain medium of the first laser supply may be argon gas. In some embodiments, a gain medium may be another material. In some embodiments, the wavelength of light output by the gain medium of the laser supply may be converted via nonlinear crystals to the desired output wavelength.

In some embodiments, a wavelength of the treatment beam may be infrared radiation, green visible light, or another wavelength. In some embodiments, the system may select a wavelength that causes microbubbles to form in the eye. In some embodiments, the system may determine the wavelength of the treatment beam, as discussed in relation to FIG. 1. The system may apply the treatment beam to a first region of an eye. In some embodiments, the first region of the eye may be an iris of the eye. The first region of the eye may be a trabecular meshwork of the eye. In some embodiments, the first region of the eye may be a retina of the eye. The system may scan the treatment beam in a pre-determined pattern (e.g., a spiral pattern surrounding the pupil or a raster pattern avoiding the pupil) about the first region of the eye.

The treatment beam may create a treatment effect in the eye. In some embodiments, the treatment effect may be a microbubble formation. A microbubble may be a tiny bubble (e.g., in the micrometer range). Removal of pigment from the target tissue may occur at the temperature at which microbubbles first occur, slightly below that temperature, or slightly above that temperature. Microbubble formation may be used to gauge the delivered dose of laser energy, and set the treatment level appropriately. These microbubbles need not be maintained for a long duration or recreated multiple times. A single exposure may be sufficient to induce denaturation of the granule. In some embodiments, microbubbles may be distinguished from other types of bubbles, such as champaign bubbles, which may be substantially larger than microbubbles and may occur at a higher radiative exposure value. Microbubble detection may be achieved by the system monitoring the target tissue surface optically or acoustically during treatment.

One embodiment of an optical microbubble monitoring system may include a video microscope using a standard 40× microscope objective through which fast flash photographs may be taken by a high-speed image device (such as the 4 Quik E ICCD nanosecond high-speed camera from Stanford Computer Optics, Berkeley, CAS, USA), a frame grabber (such as the Cyton-CXP4 from BitFlow, Woburn, MA, USA), and a 3-5 ns flash illumination source (such as the VSL-337ND-S Pulsed Nitrogen Laser from Spectra-Physics, Santa Clara, CA, USA). Another example of an optical microbubble monitoring system captures the increased light reflection from the generated bubble-water interface using confocal imaging to a photomultiplier (such as the H7827-001 photosensor module from Hamamatsu, Hamamatsu City, Japan). The system may then record the output data using a transient recorder (such as the TR40-16 bit-3U from Licel GmbH, Berlin, Germany) and transfer the recorded data to a computer (such as the TPC-2230 from NI, Austin, TX, USA) for processing and analysis. One embodiment of an acoustic microbubble monitoring system may include a hydrophone (such as the HFO-690 optical fiber hydrophone from Onda, Sunnyvale, CA, USA). Again, the output data may be recorded using a transient recorder (such as the TR40-16 bit-3U from Licel GmbH, Berlin, Germany) and transferred to a computer (such as the TPC-2230 from NI, Austin, TX, USA) for processing and analysis. In some embodiments, the system may use a combination of approaches to detect the microbubbles.

In some embodiments, microbubbles may be detected using the dual-beam approach described herein, which may be more sensitive than other methods of detecting microbubbles. Highly sensitive methods and devices should be used for real-time microbubble detection. If detection is not sufficiently sensitive, and the microbubbles are not detected when they first appear, the radiant energy may be too high, causing ablation of the melanocytes and inflammation of anterior chamber tissues. Consider, for example, the ALT and SLT laser procedures, where the laser radiation is applied to the TM, and the radiative exposure value is established by increasing the radiative energy until champaign bubbles are visible on the TM, and then reduced slightly. These champaign bubbles are substantially larger than microbubbles, and they occur at a higher radiative exposure value. Because the ALT and SLT procedures are limited to scattered clusters of melanocytes originating from the IPE and lodged in the TM, delivery of an excessive radiative exposure value and ablation of these clusters are unlikely to release a sufficient quantity of melanosomes to cause serious inflammation or injury to the eye. Then consider, by contrast, the aesthetic iridoplasty procedure, where the laser radiation is applied to the anterior iris, and the radiative exposure value is established by increasing the radiative energy until microbubbles are visible on the iris surface. Here, primarily due to the relative size of the treated area (i.e., all or a substantial portion of the iris surface, as compared to a portion of the TM), an excessive radiative exposure value and ablation of the melanocytes can cause severe inflammation and could in theory cause long-term injury.

In some embodiments, the treatment effect may be an MRE value capable of denaturing pigment granules. In some embodiments, the treatment effect may be an MRE value capable of ablating pigment granules. The MRE may be an efficacy parameter to ensure that a threshold radiative exposure value is achieved for stromal or retinal pigment elimination. The MRE may be the minimum radiative exposure value capable of denaturing the pigment granules (melanosomes) within the pigment cells (melanocytes) located primarily along the anterior surface of the iris, TM, or retina of the eye and secondarily and at lesser density within the stromal fibers of the iris of the eye or other subsurface regions of the target tissue. In some embodiments, the treatment effect may be a denaturation of at least one of melanosomes or melanocytes. In some embodiments, the treatment effect may be an ablation of at least one of melanosomes or melanocytes. In some embodiments, the treatment effect may be an eye-color change. In some embodiments, the treatment effect may be a mitigating effect of glaucoma, which may include any reduction in the severity, progression, or symptoms of glaucoma. Glaucoma may be characterized by an increase in intraocular pressure (IOP), which can lead to damage to the optic nerve and may result in vision loss. The mitigating effects for glaucoma may focus on lowering the IOP and protecting the optic nerve. In some embodiments, the treatment effect may be a mitigating effect of retinitis pigmentosa (RP). RP may be a group of genetic disorders that affect the retina's ability to respond to light, leading to a progressive loss of vision. Mitigating effects may slow the progression of RP and help patients maintain as much vision as possible for as long as possible. In some embodiments, the system may use different treatment effects or a combination of treatment effects.

Figure 2A:
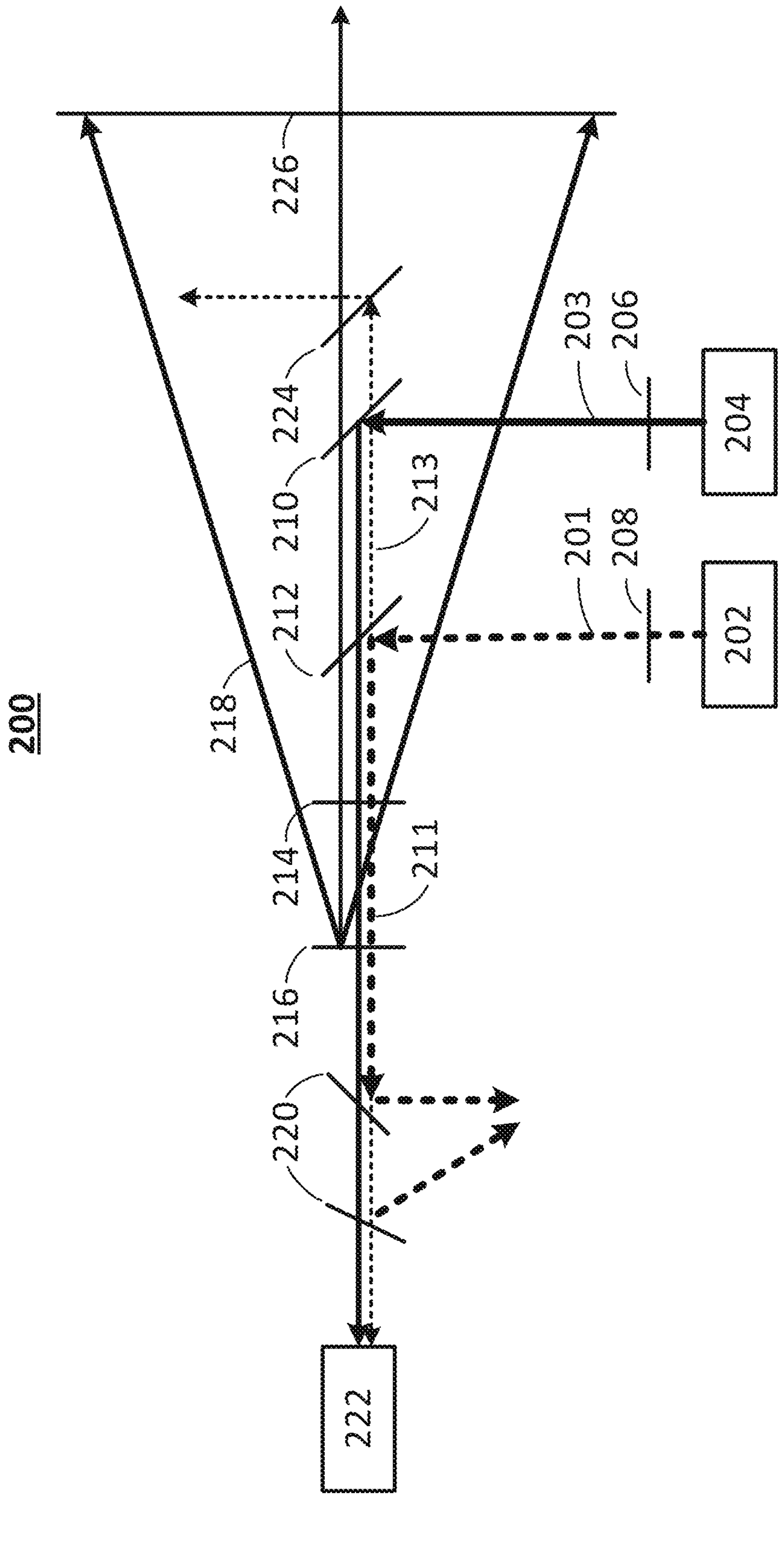
FIG. 2A shows optical beamlines for detecting microbubbles, in accordance with one or more embodiments.

FIG. 2A shows optical beamlines for detecting microbubbles, in accordance with one or more embodiments. In some embodiments, FIG. 2A may depict a configuration 200 for detecting microbubbles. A portion of configuration 200, or other configurations, may be used. Configuration 200 may include a treatment beam 201. The treatment beam may be depicted by dashed arrows in configuration 200. In some embodiments, treatment beam 201 may emanate from a first power supply 202. Treatment beam 201 may pass through a collimation lens 208. In some embodiments, collimation lens 208 may be an optical device used to shape and direct beams. For example, collimation lens 208 may take diverging or converging beams and transform them into parallel beams of light. Treatment beam 201 may be split by dichroic beam splitter 212.

Diverging beams may refer to sets of light rays or waves that spread out as they travel away from a point of origin. Unlike collimated beams, where the rays remain parallel and do not converge or diverge significantly, diverging beams exhibit an increasing angle between adjacent rays as they propagate. Diverging beams spread out over distance. The angle between neighboring rays becomes wider as the waves move away from the source. Diverging beams do not converge to a focal point. Instead, they disperse in various directions. Converging beams refer to sets of light rays or waves that come together or converge at a certain point. In contrast to diverging beams, where the rays spread out as they travel, converging beams exhibit a narrowing of the angle between adjacent rays, ultimately meeting at a focal point. Converging beams have the property of focusing, where the rays come together at a specific point called the focal point. As the beams propagate, the angle between adjacent rays decreases, leading to convergence.

Dichroic beam splitter 212 may be a specialized optical device used to separate a beam of light into two distinct beams, each containing different wavelengths or colors of light. This may be achieved through the use of dichroic filters, which reflect certain wavelengths of light while allowing others to pass through. Dichroic beam splitter 212 may split treatment beam 201 into treatment beam 211 and treatment beam 213. In some embodiments, treatment beam 213 may travel toward a dichroic blocker 224, which may direct treatment beam 213 away from the system. Dichroic blockers may be optical devices that selectively block or reflect specific wavelengths of light while allowing others to pass through. For example, dichroic blocker 224 may remove treatment beam 213 from the path along which the beams are being measured so that other light can be measured (e.g., as will be discussed in detail below). In some embodiments, treatment beam 211 may travel through focus lens 214, which may focus treatment beam 211 at a specific focal point on a sample 216 (e.g., the iris). In some embodiments, treatment beam 211 may pass through sample 216 and may be deflected by dichroic blockers 220. In some embodiments, transmission detector 222 may measure what remains of treatment beam 211. In some embodiments, configurations of the methods and systems described herein may not include features pictured to the left of sample 216 (e.g., dichroic blockers 220 and transmission detector 222). For example, a configuration may include sample 216 and features pictured to the right of sample 216.

As described herein, a beam splitter may be an optical device that divides an incoming light beam into two or more separate beams by transmitting, reflecting, or both. The specific working mechanism of a beam splitter depends on its design and type. A cube beam splitter is a type of optical prism made of a glass cube with a thin coating applied to one of its faces. The coating is usually a partially reflecting coating that allows some percentage of light to pass through (transmit) while reflecting the rest. When a light beam enters the cube from one side, it encounters the coated face. A portion of the light is transmitted through the coating while the remaining portion is reflected. The transmitted and reflected beams exit the cube at different points, resulting in two separate beams. A plate beam splitter is a thin glass or optical material with a partially reflecting coating on one surface. Light passes through the plate, and a fraction of it is transmitted while the rest is reflected. The transmitted and reflected beams emerge from the same side of the plate but travel in different directions. A key factor in the operation of a beam splitter may be the coating applied to the surface. The coating is designed to be partially reflective, allowing some light to pass through and reflecting the rest. The ratio of transmitted to reflected light can be controlled by adjusting the properties of the coating. The ratio of transmitted to reflected light may be made different at different wavelengths by design and implementation of the coating.

In some embodiments, the system may determine a first setting for the treatment beam. For example, the first setting may be a first power level of the treatment beam. In some embodiments, the system may determine a power output of the first laser supply (e.g., the first setting) before emitting the treatment beam. Laser power may mean W/cm$^2$ or J/cm$^2$, depending on the context—as they are related by the exposure time.

In some embodiments, the system may increase a power output of the first laser supply while applying the treatment beam using the first laser supply. In some embodiments, the system may determine a second setting for the treatment beam. For example, the system may cease increasing the power level of the treatment beam upon reaching the second setting. In some embodiments, the system may determine the second setting based on the treatment effect. As discussed above, the treatment effect may be, for example, formation of microbubbles. In some embodiments, microbubbles may be detected visually or acoustically. Upon detecting microbubbles forming, the system may keep the power of the treatment beam at the level causing microbubbles. In some embodiments, upon detecting microbubbles forming, the system may decrease the power of the treatment beam to a level slightly below that causing microbubbles. In some embodiments, upon detecting microbubbles forming, the system may increase the power of the treatment beam to a level slightly above that causing microbubbles. In some embodiments, the system may use the second setting for the entire target tissue surface upon determining the second seeing based on microbubble detection in one region of the target tissue surface. In some embodiments, the second setting may be determined by the user/technician and manually adjusted. In some embodiments, the second setting may be determined by the processor and automatically adjusted.

The power output of a laser can be adjusted using various methods depending on the type of laser and the specific design of the laser system. For example, many lasers operate based on a pumping mechanism where an external energy source (pump source) excites the laser medium to a higher energy state. By adjusting the power of the pump source, the rate at which the laser medium is excited can be controlled, directly influencing the laser's power output. Additionally or alternatively, some lasers have gain media with variable properties, such as semiconductor lasers or certain types of solid-state lasers. By controlling the properties of the gain medium, such as the current passing through a semiconductor laser, the population inversion and, hence, the laser output power can be adjusted. Additionally or alternatively, Q-switching is a technique that May be used to produce short and high-power pulses from a laser. It involves quickly modulating the quality factor (Q) of the laser cavity. By momentarily preventing the lasing action and then allowing it to occur, a buildup of energy can be achieved, leading to a high-power output when the laser is finally "switched on." Additionally or alternatively, the output coupler in a laser cavity can be modulated to control the amount of light that is allowed to exit the cavity. By adjusting the reflectivity of the output coupler or using an electro-optic modulator, the power output of the laser can be controlled. Additionally or alternatively, the performance of some lasers is temperature-dependent. By controlling the temperature of the laser components, such as the gain medium or resonator mirrors, the laser output can be tuned. Additionally or alternatively, attenuators can be introduced into the laser beam path to reduce its intensity. Variable attenuators can be adjusted to control the laser power output. Additionally or alternatively, the laser system may incorporate feedback control mechanisms to automatically adjust parameters like pump power or cavity conditions to maintain a constant output power.

In some embodiments, first power supply 202 may apply treatment beam 201 in pulses. For example, laser pulse widths may be in the nanosecond range (i.e., from below 1 nanosecond to 1 microsecond). For example, each pulse of treatment beam 201 may last 20 nano seconds. The pulse repetition rate may be in the kilohertz range (i.e., from below 1 kHz to 1 MHz). Some embodiments may have a pulse width between 5 ns and 300 ns, which may provide improved pigment denaturation. Q-switching may be utilized as a pulsing method, as it tends to be suited to the nanosecond pulse width. Some embodiments include active Q-switching with a modulator device. In some embodiments, each pulse may be over by the time microbubbles would begin to form as a result of that pulse. In some embodiments, following each pulse of treatment beam 201, the system may monitor for the formation of microbubbles (e.g., as discussed below in greater detail). If no microbubbles are detected, first power supply 202 may apply another pulse at a higher power level. The system may again monitor for the formation of microbubbles. This process may repeat until the system detects microbubbles. In some embodiments, the system may distinguish the first setting and the second setting based on treatment beam characteristics. For example, the treatment beam characteristics may be a wavelength, a color, a collimated beam, a beam angle, a beam diameter, beam dimensions, a contribution of the treatment beam to the backscatter pattern, or a combination of characteristics.

In some embodiments, the system may include a second laser supply that emits a probe beam. For example, a probe beam may be a secondary beam of light that is used to investigate or measure a sample or a region of interest. The probe beam may be used in conjunction with another primary beam, often called the treatment beam, pump beam, or excitation beam. Together, these beams provide information about the properties of the sample. In some embodiments, a wavelength of the probe beam may be infrared radiation, red visible light, or another wavelength. In some embodiments, the wavelength of the probe beam may be different than the wavelength of the treatment beam. In some embodiments, a polarization of the probe light may be different than the polarization of the treatment beam. In some embodiments, a diameter of the probe beam may be a percentage of a diameter of the treatment beam. For example, the diameter of the probe beam may be 1%-500%, or another percentage of the diameter of the treatment beam. In some embodiments, the diameter of the probe beam may be the same as the diameter of the treatment beam to maximize backscatter of the probe beam when microbubbles form. In some embodiments, the probe beam may be aligned with the treatment beam, with the incidence angle of the probe beam being on axis with the treatment beam. In some embodiments, the probe beam may be at an angle relative to the treatment beam, with the incidence angle of the probe beam being less than or equal to 75°. In some embodiments, a gain medium of the second laser supply may be semiconductor materials layered to form a diode. In some embodiments, a gain medium of the second laser supply may be argon gas. In some embodiments, a gain medium may be another material.

The system may apply the probe beam to a second region of the eye. In some embodiments, the system may scan the probe beam in a pre-determined pattern (e.g., a spiral pattern surrounding the pupil or a raster pattern avoiding the pupil) about a second region of the eye. In some embodiments, the second region of the eye includes the first region of the eye that is scanned in the pre-determined pattern by the treatment beam. In some embodiments, the probe laser may detect microbubbles when the second region overlaps the first region. In some embodiments, the system determines a power output of the second laser supply (e.g., second power supply 204) before applying the treatment beam. For example, the system may determine an initial setting for the probe beam. The system may increase a power output of the second laser supply while applying the probe beam using the second laser supply.

Returning to FIG. 2A, configuration 200 may include a probe beam 203. The probe beam may be depicted by solid arrows in configuration 200. In some embodiments, probe beam 203 may emanate from a second power supply 204. Probe beam 203 may pass through a collimation lens 206. In some embodiments, collimation lens 206 may be an optical device used to shape and direct beams. For example, collimation lens 206 may take diverging or converging beams and transform them into parallel beams of light. Probe beam 203 may then travel a beam splitter 210. Beam splitter 210 may, for example, be a 50/50 beam splitter, which is an optical device that splits an incoming light beam into two beams of equal intensity. A 50/50 beam splitter may divide the light such that 50% of the light is transmitted through the splitter, while the other 50% is reflected. Probe beam 203 may then travel to sample 216. As shown in configuration 200, the probe beam may be aligned with the treatment beam, with the incidence angle of the probe beam being on axis with the treatment beam. In some embodiments, the probe beam may be at an angle relative to the treatment beam. Before microbubbles form, probe beam 203 may travel through sample 216 to transmission detector 222. In some embodiments, probe beam 203 may travel into sample 216 without being backscattered. Once microbubbles form, probe beam 203 may be backscattered by the microbubbles (e.g., backscatter 218).

In some embodiments, the system includes a backscatter detector, which detects a backscatter pattern (e.g., detects and/or measures backscattered radiation or particles). The backscatter detector may include an optical sensor with an optical filter that passes the probe beam and limits passage of other light. In some embodiments, the probe beam creates a backscatter pattern based on detected microbubbles. For example, when microbubbles form in the eye, the probe beam may scatter backward and outward after contacting the microbubbles, in the direction of the backscatter detector. The backscatter detector may detect a pattern of the reflected light, and the pattern may indicate whether the microbubbles have formed. In some embodiments, the backscatter pattern may be a pattern in space, a pattern in time, a pattern in both space and time, or a different type of pattern. Configuration 200 may include a backscatter detector 226. Configuration 200 depicts backscatter 218 directed toward backscatter detector 226. Thus, to detect microbubbles once the microbubbles form, backscatter detector 226 detects probe beam 203 being reflected backward from sample 216. In some embodiments, probe beam 203 creates a backscatter pattern based on detected microbubbles. For example, when microbubbles form in the eye, probe beam 203 may be reflected backward and outward after contacting the microbubbles. Backscatter detector 226 may detect a pattern of the reflected light, and the pattern may indicate that the microbubbles have formed.

Figure 2B:
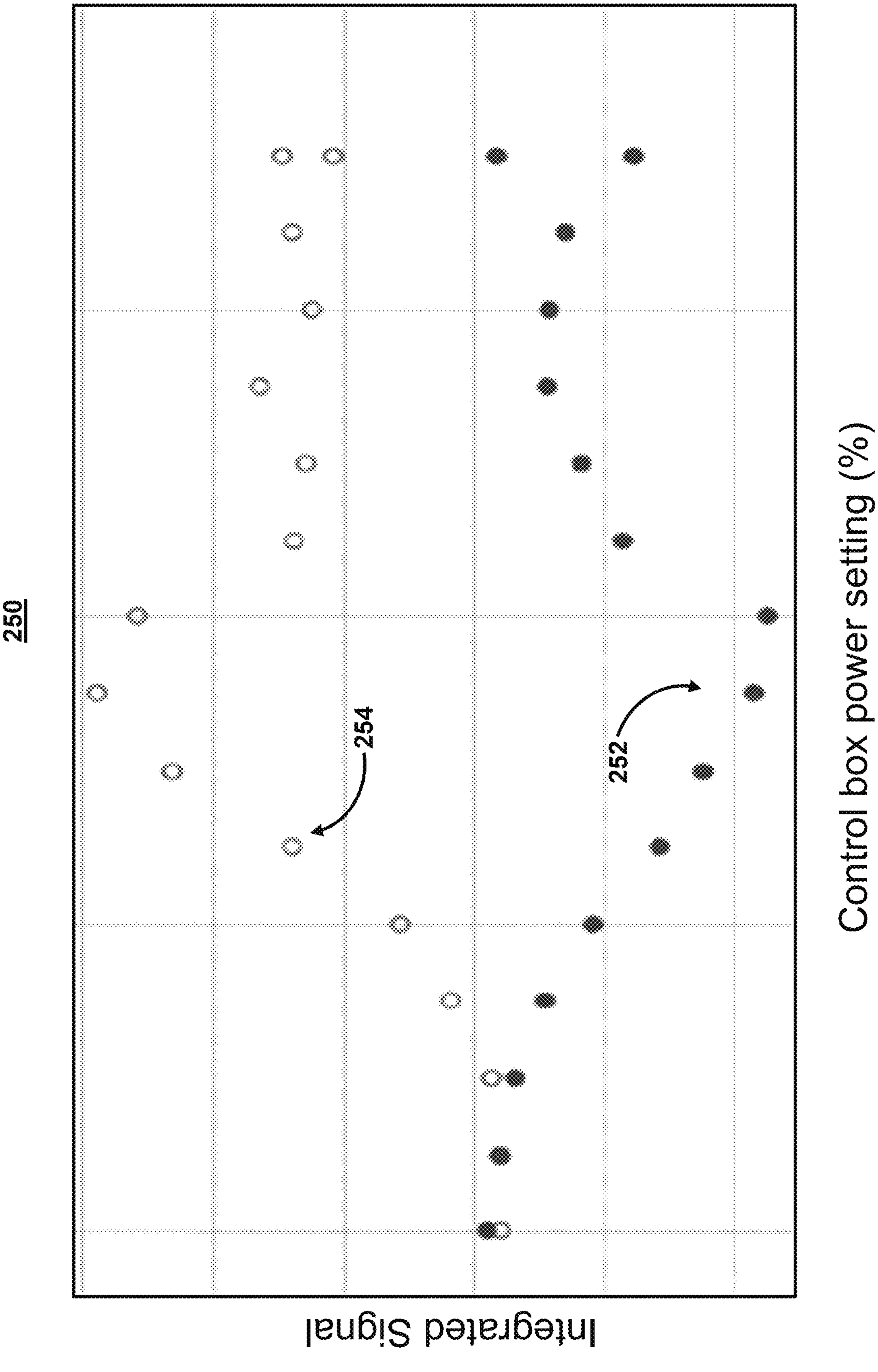
FIG. 2B shows a backscatter chart, in accordance with one or more embodiments.

FIG. 2B shows a backscatter chart 250, in accordance with one or more embodiments. For example, backscatter chart 250 may illustrate the probe beam (e.g., probe beam 203) being both transmitted and backscattered (e.g., detected by backscatter detector 226) by microbubbles forming in the eye (e.g., sample 216). For example, once microbubbles form, transmitted probe 252 may decrease and backscattered probe 254 may increase. The microbubbles may then change in size or pop, causing backscattered probe 254 to increase or decrease as the backscatter pattern changes. The backscatter detection depicted by backscatter chart 250 may be used to detect microbubbles and determine a power setting for the treatment beam.

In some embodiments, backscatter detector 226 may detect backscattered light from probe beam 203 that is reflected at an angle (e.g., backscatter 218). The microbubbles may reflect probe beam 203 in various directions, causing a spray of light toward backscatter detector 226. In some embodiments, focus lens 214 may collimate backscatter 218 so that the backscattered light is not lost as it travels toward backscatter detector 226. In some embodiments, the backscatter pattern may indicate a size of the microbubbles forming in the eye. In some embodiments, the backscatter pattern may indicate a density of one or more groups of microbubbles. In some embodiments, the backscatter pattern may indicate a duration associated with one or more microbubbles (e.g., before the microbubbles burst).

In some embodiments, the system further includes a processor configured to determine the treatment effect based on the backscatter pattern. For example, the backscatter pattern may be a change indicating that a treatment effect is occurring. For example, the backscatter pattern may be a threshold pattern change indicating that the treatment effect (e.g., microbubble formation) is occurring. In some embodiments, the backscatter pattern includes a profile value of the beam profile of the backscattered probe beam. After microbubbles form, the profile value may indicate that the treatment effect is occurring. The processor may determine that the treatment effect is occurring based on any of the aforementioned patterns or based on a combination of patterns. In some embodiments, the treatment beam may contribute to the backscatter pattern, and in some embodiments the treatment beam may not contribute to the backscatter pattern.

In some embodiments, the system further includes a power modulator configured to modulate a power level of the first laser supply based on the treatment effect determined by the processor. For example, as previously discussed, the system may set the power level of the treatment beam based on the level at which microbubbles form. In some embodiments, the system may set the power level of the treatment beam to be equal to the level at which microbubbles form. In some embodiments, the system may set the power level of the treatment beam to be slightly less than the level at which microbubbles form. In some embodiments, the system may set the power level of the treatment beam to another level.

Exemplary optical power modulators may include acousto-optic modulators, electro-optic intensity modulators, electro-absorption modulators, semiconductor optical amplifiers, and liquid crystal modulators. A structural embodiment of an exemplary acousto-optic modulator may include a transducer that generates a sound wave that partially diffracts the laser beam. A structural embodiment of an exemplary electro-optic intensity modulator may include a Pockels cell between two polarizers. The Pockels cell modulates the phase of the beam, and the polarizers transform the phase modulation into an intensity modulation. The Pockels cell may have a single crystal or two or more crystals to reduce its power requirements. The polarizers may be replaced by an interferometer, as in the case of a Mach-Zehnder modulator. The power modulator may thus modulate the power of the treatment beam using a Pockels cell. A structural embodiment of an exemplary electro-absorption modulator may include one or more semiconductor devices operating on the Franz Keldysh effect. Such modulators may operate on light in a waveguide and may be coupled to optical fibers or placed on a chip together with other components, such as a laser diode to form a telecom transmitter. An exemplary semiconductor optical amplifier used as an intensity modulator includes a semiconductor optical amplifier with or without drive current. Without drive current, the amplifier provides some degree of attenuation as negative gain. When supplied with pump current, attenuation is achieved as positive gain. An exemplary liquid crystal modulator applies a voltage to a liquid crystal material to modulate light polarization and obtain intensity modulation by adding a polarizer.

In some embodiments, the system may repeat the aforementioned processes to determine the power level of the treatment beam at each session. For example, eye change procedures may be performed over several sessions, and the eye may be lighter at each session. Thus, the correct power level may be different for each session. The methods and systems described herein may use microbubbles to determine, at any given session, the correct power level to safely change the color of the eye in its current state.

Figure 3:
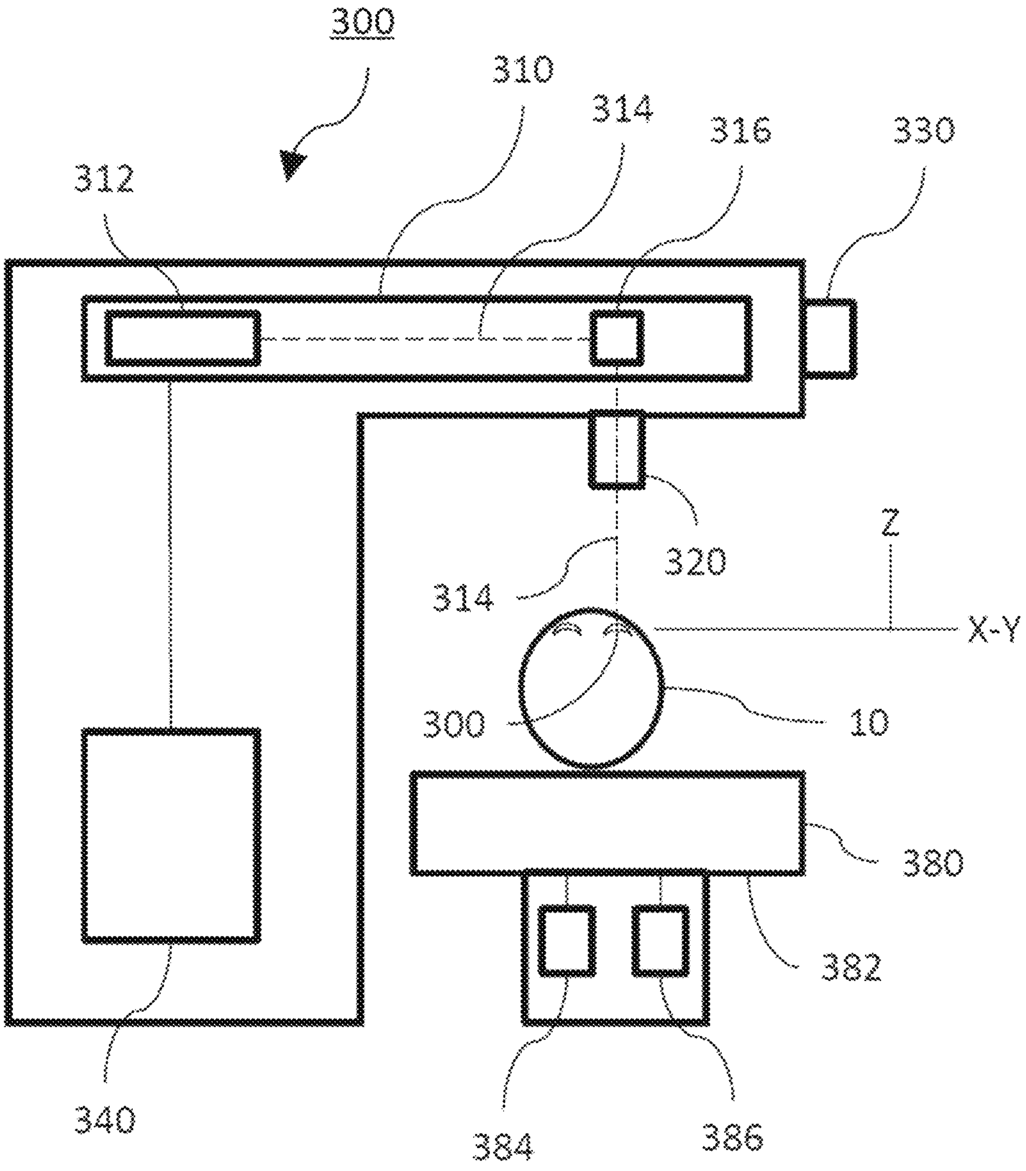
FIG. 3 shows a simplified diagram of a laser system and patient positioning system, in accordance with one or more embodiments.

FIG. 3 shows a simplified diagram of a laser system and patient positioning system, in accordance with one or more embodiments. One embodiment of the overall system 300 may include the laser system 310 and a patient positioning system 380. The head of patient 10 (with eyes 100) is shown supported by the patient positioning system in a location suitable for the iris color alteration procedure. Laser system 310 may include the laser head 312, which provides laser light 314. The laser head may include components to generate laser light at varying wavelengths, for example, at 1064 nm or 532 nm (Nd:YLF or Nd:YAG). In some embodiments, laser head 312 may represent multiple laser power supplies (e.g., first power supply 202 and second power supply 204, as shown in FIG. 2A) emitting multiple laser lights 314 (e.g., treatment beam 201 and probe beam 203, as shown in FIG. 2A).

The laser head may include an energy source (aka a pump or pump source), a gain medium, and two or more mirrors that form an optical resonator. Exemplary energy sources include electrical discharges, flashlamps, arc lamps, output from another laser, and chemical reactions. Exemplary gain media include liquids (e.g., dyes comprising chemical solvents and chemical dyes), gases (e.g., carbon dioxide, argon, krypton, and helium-neon), solids (e.g., crystals and glasses, such as yttrium-aluminum garnet, yttrium lithium fluoride, sapphire, titanium-sapphire, lithium strontium aluminum fluoride, yttrium lithium fluoride, neodymium glass, and erbium glass), which may be doped with an impurity (e.g., chromium, neodymium, erbium, or titanium ions) and may be pumped by flashlamps or output from another laser; and semiconductors, with uniform or differing dopant distribution (e.g., laser diode), which may be pumped by electrical current.

Embodiments of the laser head may include an optical frequency multiplier (e.g., a frequency doubler and sum-frequency generator), where the laser output frequency is increased by passing it through a non-linear crystal or other material. The benefit of an optical frequency multiplier is that it increases the range of frequencies/wavelengths available from a given gain medium. The non-linear material may be inserted into the optical resonator for one-step frequency multiplication, or the fundamental (i.e., non-multiplied) output beam may be passed through the non-linear material after leaving the optical resonator for two-step frequency multiplication. Exemplary non-linear materials for frequency doubling may include: lithium niobate, lithium tantalate, potassium titanyl phosphate, or lithium triborate. Two-step frequency tripling is typically performed by frequency doubling a fraction of the fundamental output beam in a first step. The doubled fraction of the fundamental beam and the non-doubled remainder of the fundamental beam are then coupled into a second non-linear frequency tripling material in a second step for sum-frequency mixing. Exemplary non-linear materials for frequency tripling may include potassium dihydrogen phosphate.

One combination of gain medium and optical frequency multiplier is Nd:YAG with a frequency doubler. The natural harmonic of a laser beam generated by an Nd:YAG gain medium is a wavelength of 1,064 nm, which is then halved to 532 nm by the frequency doubler. This wavelength may be utilized as (a) it falls within the visible light spectrum (i.e., green), thereby passing through the clear cornea with little or no absorption; (b) it has a high absorption coefficient in pigment, thereby effecting selective photothermolysis in the pigmented target tissue; and (c) the wavelength is relatively short, thereby limiting the depth of penetration and avoiding unwanted damage to the IPE. Any other combination of gain media and optical frequency multiplication that meets these three criteria may also be implemented in some embodiments.

Galvos systems 316 (also referred to as the x-y beam guidance system) may be included in the laser system and may include adjustable mirrors to provide a means of delivering the laser light to various locations on an X-Y plane (typically the plane of the target tissue surface where the laser light is usually focused). Further implementations of the laser system may include, for example, range-finders and/or optical tracking systems, which may include cameras to determine an X-Y deviation of the center of the eye relative to the optical axis of the laser system.

In some embodiments, the x-y beam guidance system may scan the beam spot about the target tissue surface. The scanning parameters may include the size, shape, and position of the target region, the line and spot separation between each beam spot, and the predetermined scan pattern. The computer imaging software may determine the size, shape, and position of the target region based upon target tissue images captured by the x-y imaging system and transmitted to the computer for processing. Once processed, the size, shape, and position data may be transmitted to the scanning program to drive the x-y beam guidance system. New target tissue images may be captured at predetermined intervals and transmitted to the computer for processing throughout the procedure. Captured images are compared, and if they indicate a change in target tissue position, the computer imaging software calculates the x-y deltas and transmits the shift coordinates to the scanning program, which in turn executes the shift in the scanning position. The line and spot separation between each beam spot may be predetermined and programmed into the scanning program prior to treatment. In some cases, the spot and line separation place each beam spot tangent to the others throughout the target region. The scan pattern may be raster (including slow-x/fast-y and slow-y/fast-x), spiral (including limbus to pupil and pupil to limbus), vector, and Lissajous scans.

In one embodiment, the x-y beam guidance system may scan the beam spot about the target tissue surface by means of controlled deflection of the laser beam. Embodiments utilizing beam steering in two dimensions may drive the beam spot about the two-dimensional surface of the target tissue. Beam motion may be periodic (e.g., as in barcode scanners and resonant galvanometer scanners) or freely addressable (e.g., as in servo-controlled galvanometer scanners). Exemplary beam steering in two dimensions may include: rotating one mirror along two axes (e.g., one mirror scans in one dimension along one row and then shifts to scan in one dimension along an adjacent) and reflecting the laser beam onto two closely spaced mirrors mounted on orthogonal axes.

There are numerous methods for controlled beam deflection, both mechanical and non-mechanical. Exemplary non-mechanical methods may include steerable electro-evanescent optical refractor or SEEOR, electro-optical beam modulation, and acousto-optic beam deflection. Exemplary mechanical methods may include nanopositioning using a piezo-translation stage, the micro-electromechanical system or MEMS controllable microlens array, and controlled deflection devices. Mechanically controlled deflection devices may include motion controllers (e.g., motors, galvanometers, piezoelectric actuators, and magnetostrictive actuators), optical elements (e.g., mirrors, lenses, and prisms), affixed to motion controllers, and driver boards (aka servos) or similar devices to manage the motion controllers. The optical elements may have a variety of sizes, thicknesses, surface qualities, shapes, and optical coatings, the selection of which depends upon the beam diameter, wavelength, power, target region size and shape, and speed requirements. Some embodiments may utilize optical elements that are flat or polygonal mirrors. An embodiment of the motion controller may include a galvanometer, including a rotor and stator (to manage torque efficiency) and a position detector (PD) (to manage system performance). An exemplary PD may include one or more illumination diodes, masks, and photodetectors. Driver boards may be analog or digital. Scan motion control might also comprise one or more rotary encoders and control electronics that provide the suitable electric current to the motion controller to achieve a desired angle or phase. The installed scanning program disclosed above may be configured to collect measured scan and target region data. In some embodiments, the system may use either the same steering system or different steering systems to direct the probe beam and the treatment beam.

The x-y beam guidance system may apply the laser spot to all or any portion of the anterior target tissue surface. Treated fractions of the anterior target tissue surface may include the following (which are inclusive and do not take into account any spared tissue due to line and/or spot separations): greater than ¼; greater than 30%; greater than ⅓; greater than ½; and greater than ¾.

The system can include one or types of range-finding apparatuses to measure the Z distance from a reference point to the target (e.g., the target tissue surface). As used herein, the Z direction is taken to be the vertical direction, perpendicular to the X-Y plane (e.g., the target tissue surface). A component referred to herein as optical exit 320 may be provided to allow the exiting of laser light to reach the eye. Optical exit 320 may include windows, lenses (e.g., dichroic lenses), mirrors, shutters, or other optical components. In some implementations, the system may include platform control 330, which may be configured to provide coarse adjustment (manually or automatically computer-controlled) in the X, Y, or Z directions. The platform control 330 may also be configured to perform fine adjustments similar to the above, with such fine adjustments implemented by computer control. Also included in some implementations are control computer and power supplies, depicted by element 340 in FIG. 3. Alternatively, control computers or electronics and some or all of the needed power supplies need not be contained in the system 300 as depicted in FIG. 3, but may be distributed in other locations or networked to be operatively connected to the laser system. Examples of range-finding apparatuses may include systems that perform triangulation, time-of-flight measurements, etc., with one specific example being an optical coherence tomography system. Further discussion of range-finding and/or tracking apparatuses is provided throughout the application, such as in the discussion of FIG. 3.

Patient positioning system 380 is shown in the simplified diagram as containing patient support 382. Examples of patient support may include a flatbed, recliner, couch, head or neck brace, etc. Control of the patient positioning system may be realized by, for example, X-Y actuator 384 and/or Z actuator 386, which may be configured to move the patient in the respective directions for optimal alignment with the delivered laser light.

Figure 4A:
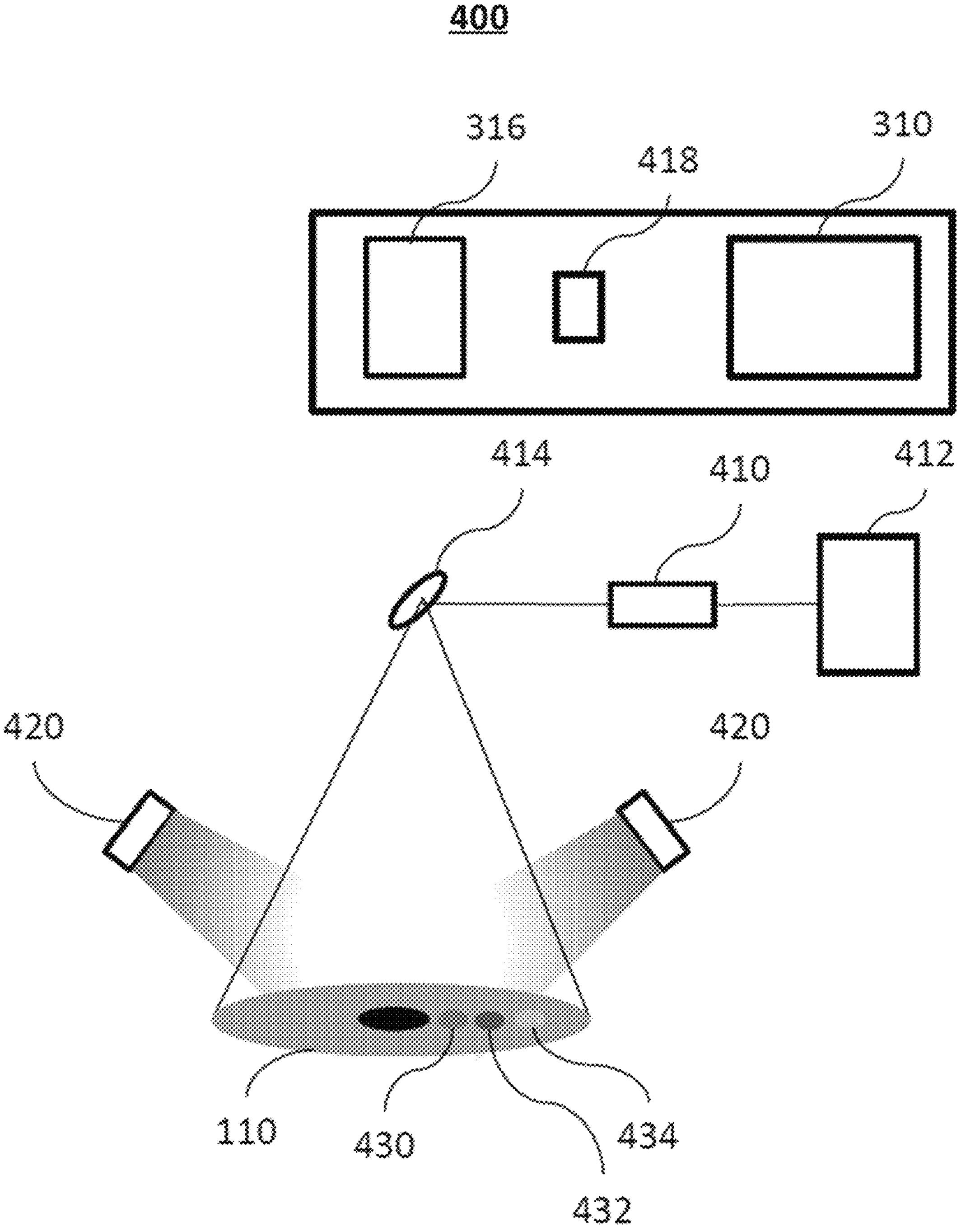
FIG. 4A shows a simplified diagram of a laser system and image sensor for use in mapping the iris, in accordance with one or more embodiments.

FIG. 4A shows a simplified diagram of a laser system 400 and image sensor 410 for use in mapping the target tissue, in accordance with one or more embodiments. Determination of the proper laser power may depend on variations in the absorption of the delivered laser power due to inhomogeneities in regions 430, 432, 434 of the pigment layer. Such variations may be caused by, for example, varying density of the pigment, varying sizes of pigment cells, types and compositions of the pigment, etc. As such, regions of the target tissue where the pigment has a higher absorption coefficient reach a higher temperature (or a target temperature faster) for a given laser power. These differences, if not accounted for, may result in uneven target tissue color alteration or possibly even damage to the eye. To address this problem, some implementations of the disclosed methods may include imaging the target tissue with an image sensor operatively connected to a computer 412 prior to the procedure to generate images of the target tissue. Examples of image sensors may include a CCD, COMS, or camera used in conjunction with an illumination source 420, wherein the wavelength range of the sensor includes the wavelength of the illumination source. Exemplary wavelengths include near and mid-infrared, visible light, or the specific wavelength of the treatment laser beam. An embodiment might also include software programs capable of creating a digital color model from the captured images and mapping or otherwise analyzing the pigment absorption coefficients for the treatment wavelength based on the model. Exemplary digital color models include RGB (which stands for red-green-blue), HSI (for hue-saturation-intensity), HSL (for hue-saturation-lightness), HSV (for hue-saturation-value), CMY (for cyan-magenta-yellow), and YIQ (luminance-inphase-quadrature).

To facilitate integration of the image sensor with existing laser systems, the image sensor may incorporate a dichroic optic 414 (e.g., a dichroic lens, mirror, or prism) to divert incoming light reflected from the target tissue to the reflective or refractive side of the optic and direct it to the image sensor while allowing outgoing laser light to pass through the optic to the target tissue surface for treatment. Such implementations have the advantage that the light may be collected on the same optical axis as the laser system. This has the advantage of both simplifying and making more accurate the generation of the mapping relative to the geometry of laser system because it avoids the need to account for an off-axis image sensor.

Based on the images, a mapping of the target tissue may be generated by the system and may contain regions corresponding to varying absorption coefficients of a treatment wavelength in the pigment of the target tissue. As shown in FIG. 4A, regions 430, 432, 434 of the iris are depicted to indicate different absorption coefficients. The mapping may be, for example, 2D (or 3D) data having pixels or voxels of the imaged target tissue with each pixel or voxel having a corresponding calculated absorption coefficient. The mapping need not be stored at the pixel/voxel level but may also be in terms of larger regions (e.g., combining pixels/voxels that may have similar absorption coefficients (e.g., utilizing a watershed algorithm)). In other embodiments, regions may be specified at the subpixel/voxel level by performing 2D (or 3D) interpolation of neighboring pixels/voxels to provide a continuous function of absorption across a pixel/voxel.

As mentioned above, generating the mapping may include calculating absorption coefficients at the wavelength of the laser light in various regions of the target tissue. The present disclosure contemplates numerous implementations for calculating the absorption coefficients. For example, the image sensor (or data obtained with such) may measure the absorption or reflectivity of predetermined wavelengths within the image of the target tissue to determine the absorption coefficients. The fluence needed to increase the temperature in the target pigment and thereby initiate the biological reaction necessary to remove the target pigment is a direct function of the absorption of the energy of the laser light in the pigment. Thus, by determining the absorption coefficient of the pigment in a particular region for the given wavelength, the system can accurately determine and deliver the laser power needed for pigment removal.

The system may include various apparatuses for determining the absorption coefficients, such as those used with hyperspectral imaging (HSI) and scanning electron microscopy (SEM) images with color modeling (e.g., RBG, HSI, HSL, HSV, CMY, and YIQ) using filters appropriate for the laser wavelength.

To map the pigment density, various kinds of light may be used by the system—for example, infrared or visible. In some implementations, the saturation channel of an iris image may provide a very good estimate of pigment density. In other embodiments, the system may use blue or green channels of the image. In yet other embodiments, the system may use monochrome infrared for an approximation of pigment.

Specifically, in some embodiments, the reflectivity of the image is based on an inverse of the saturation in the image. The system may determine reflectivity, saturation, etc., on a pixel by pixel basis or over wider regions of the image. For example, based on analyzing intensities of received light at the imaging sensor, the system may break up the target tissue into regions of similar intensities (e.g., within 1%, 5%, 10%, etc.). The system may determine the average reflectivity and/or saturation of these regions for determining the absorption coefficient for all points of delivery of light in that region.

Several optional features are disclosed to aid in obtaining more accurate measurements for determining absorption coefficients. First, the illumination source may have the same (or approximately the same—e.g., within 5% or 10%) of the wavelength delivered by the laser system. For example, if the planned treatment incorporates a 1064 nm laser, then the illumination source may provide infrared light covering that wavelength. Similarly, if the laser wavelength is to be 532 nm (green), then the illumination source may provide green light. Also, in certain implementations, this imaging may further include filtering the reflected light received from the pigment at the image sensor through a bandpass filter configured to pass a wavelength corresponding to the laser light and/or illumination source. In yet other implementations, the system may include a similar bandpass filter at the illumination source, for example, if such sources are more broad-spectrum than desired.

The laser system may also include a power modulator 418 to vary the laser power based on the determined mapping. Exemplary optical power modulators may include acousto-optic modulators, electro-optic intensity modulators, electro-absorption modulators, semiconductor optical amplifiers, and liquid crystal modulators, as previously discussed.

Figure 4B:
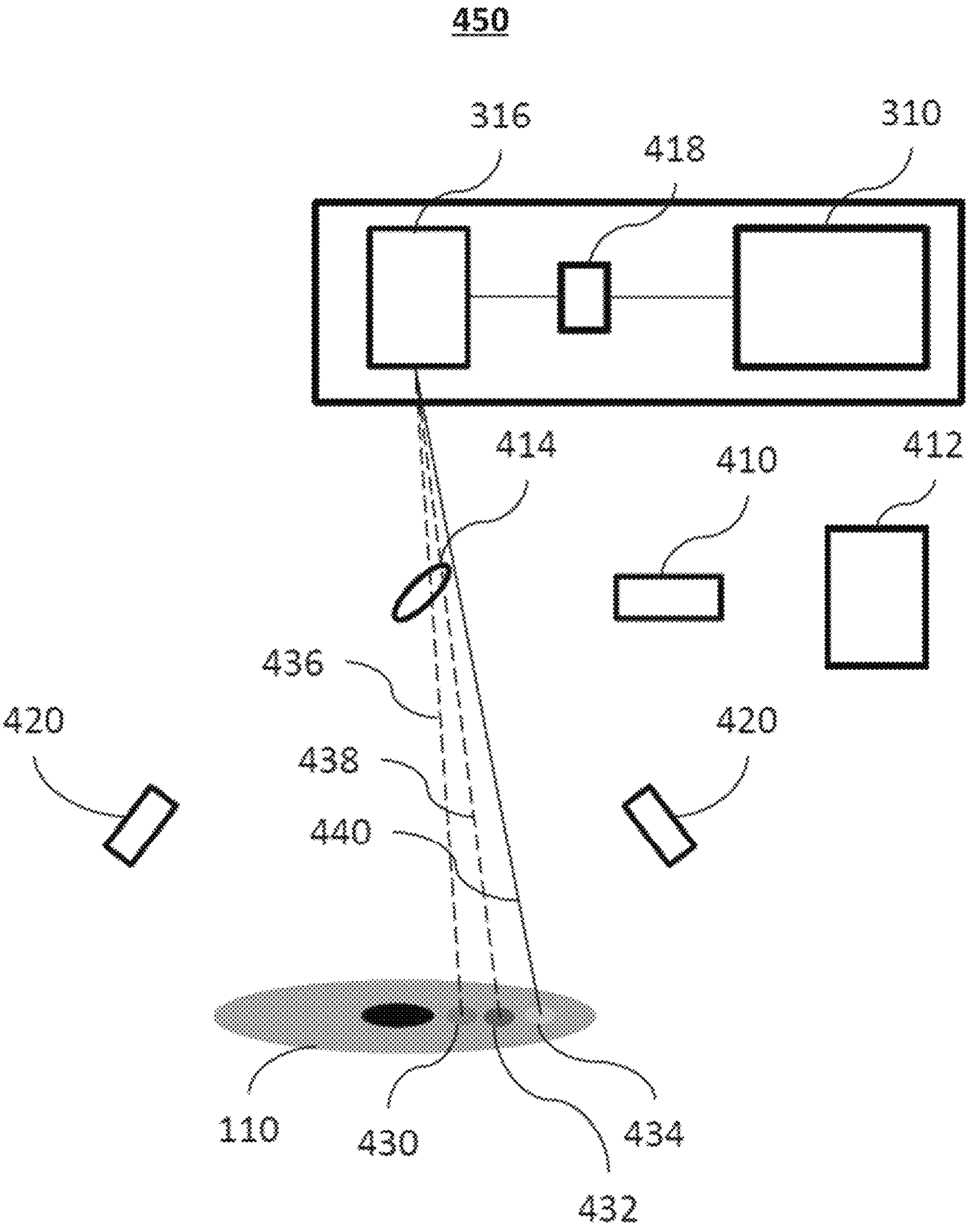
FIG. 4B shows the system of FIG. 4A delivering variable laser power to regions of the iris, in accordance with one or more embodiments.

FIG. 4B shows the system 450 of FIG. 4A delivering variable laser power to regions of the iris in accordance with one or more embodiments. With the mapping derived as noted herein, the power modulator may control delivery of laser power that accounts for the regions having different absorption coefficients. As the laser light scans the target areas of the iris, when a region is reached that has a different absorption coefficient, the system may control the power modulator to adjust the laser power accordingly. For example, the system may set the laser power based on the mapping such that regions of higher absorption coefficients receive a lower laser power than regions of lower absorption coefficients. This is depicted by exemplary laser beams 436, 438, and 440 which correspond to the regions 430, 432, and 434. The system may modulate the laser power delivered with such beams utilizing the power modulator described above.

The system may also be configured for blanking the beam wherever there is little or no pigment. Beam blanking can be accomplished in a number of ways, including deactivating the laser, deflecting the beam into a beam dump using an optic such as a prism or mirror, or reducing the radiative power to a subclinical level using the energy modulator disclosed elsewhere in this application. Deactivating the laser may, in some cases not be utilized due to time delays and other potential complications upon reactivation.

In one embodiment, anterior target tissue regions are selected or deselected for blanking automatically by illuminating the anterior target tissue using a CCD or other camera to capture an image of the anterior target tissue surface, transmitting the image to a computer with an image analysis software program (such as Celleste Image Analysis Software, Thermo Fisher Scientific Inc., Waltham, MA, USA), identifying the pigmented regions, generating a lookup table comprising the coordinate ranges of the pigmented regions, and coordinating with the beam guidance software and energy disruption or modulation software to blank the treatment beam everywhere outside of the pigmented regions.

In an alternate embodiment, anterior target tissue regions may be selected or deselected for blanking manually or automatically by the system illuminating the anterior target tissue, capturing a still or moving image using a CCD or other camera, displaying the image on the user interface touchscreen, inviting the operator to outline the regions he or she wishes to blank or irradiate, and inviting the operator to elect (e.g., via icons on a GUI displayed on the same screen) whether the outlined areas are to be treated or blanked. The display computer and software may display the operator-drawn outlines on the display, generate a lookup table comprising the coordinate ranges of the outlines, and coordinate with the beam guidance software and energy disruption or modulation software to blank the treatment beam everywhere inside or outside (as selected) of the outlined regions.

One of the advantages of these selective beam blanking implementations is that without it, re-treating the anterior target tissue surface after the pigment has been removed might result in the elimination of additional pigment from within the target tissue, which, as discussed herein, will likely increase color saturation, which might be contrary to the patient's preferences.

Some implementations of the disclosed methods may include utilizing a range-finder as part of the optical tracking system to provide accurate distances to the target location in the eye. For example, the range-finder may determine a distance between the target tissue and a reference component of the optical tracking system. In some embodiments, the range-finder may determine a distance between a target tissue (e.g., the iris, retina, or trabecular meshwork) and the reference component of the optical tracking system. Examples of reference components may include the last optical component in the laser system (e.g., a window or lens closest to the patient), a mirror or galvos, or any other component or location in the laser system with a known location to provide a point of reference for the range-finding.

Based on the determined distance, the system may control the shift of the focal point of the laser beam to remain substantially in focus between an anterior surface and posterior surface of the target tissue, at the pigment targeted for removal, or at any of the disclosed possible focusing planes. Examples of range-finders may include, for example, triangulation lasers, time-of-flight detectors, phase shift detectors, ultrasonic detectors, frequency modulation detectors, interferometers, a camera, or a light sensor.

Triangulation may utilize lasers for distance measurements. Structural embodiments of exemplary triangulation methods may include three elements: an imaging device, an illumination source, and either an additional imaging device or an additional illumination source. Illumination source(s) may include image projectors that project light images onto the iris, sclera, or other patient field. Exemplary light images might include circles and lines. In one embodiment, the laser beam may illuminate a point on the surface of the target (e.g., the iris, the sclera, or some other point on the patient's face). Diffuse or specular reflections from the illuminated point may be monitored with a position-sensitive detector, which may be placed at a given distance from the laser source such that the laser source, the target point, and the detector form a triangle. Assuming the beam incidence angle to the target is 0°, the position-sensitive detector identifies the incidence angle of the detector to the target, and the distance between the laser source and the detector is known. The distance from the laser source to the target may be determined with the appropriate trigonometric function.

Time-of-flight or pulse measurements may measure the time of flight of a radiation pulse from the measurement device to the target and back again. Exemplary forms of radiation include light (e.g., near-infrared laser) and ultrasound. An exemplary time-of-flight apparatus includes a radiation source, a radiation sensor, and a timer. Time of flight may be measured based upon timed pulses or the phase shift of an amplitude modulated wave. In the case of timed pulses, the speed of the radiation is already known, so the timer measures the turnaround time of each pulse to determine the distance, where distance=(speed of radiation×time of flight)/2.

The phase shift method may utilize an intensity-modulated laser beam. The phase shift of intensity modulation may be related to the time of flight. Compared with interferometric techniques, its accuracy is lower, but it allows unambiguous measurements over larger distances and is more suitable for targets with diffuse reflection. For small distances, ultrasonic time-of-flight methods may be used, and the device may contain an aiming laser for establishing the direction of the ultrasonic sensor but not for the distance measurement itself.

Frequency modulation methods may include frequency-modulated laser beams, for example with a repetitive linear frequency ramp. The distance to be measured may be translated into a frequency offset, which may be measured via a beat note of the transmitted and received beam.

Interferometers may be implemented for distance measurements with an accuracy that is far better than the wavelength of the light used.

Various systems for range-finding may provide very accurate measurements, for example, determining distances with the resolution of at least 10-20 μm. Such systems may include, for example, a time-domain optical coherence tomography system or a spectral domain optical coherence tomography system.

Utilizing the disclosed range-finding, some methods may utilize the same structure to include autofocusing the laser system in response to changes in the determined distance and corresponding shifts in the focal point of the beam. Computer systems in communication with the laser system may automatically autofocus the laser system and measure a distance to the pigment of the target tissue at periodic intervals (e.g., at approximately 1 kHz, 10 kHz, 100 kHz, etc.).

Exemplary methods for lens focusing include manually or electronically (a) shifting the position of one or more focal lenses (e.g., a lens mounted on a motor stage to shift along the beam access), (b) shifting the position of one or more focal mirrors (e.g., by adding a third mirror to a galvos beam steering system), (c) changing the shape of one or more focal lenses or mirrors, (d) deflecting or refracting a beam by means of an acousto-optical or electro-optical devices, (e) using electrostatic or electromagnetic lenses or mirrors to shift the focal position of the beam, or (f) moving the effective source location (e.g., the tip of the delivery fiber) with respect to the beam focusing optics.

Movement of the patient's head and eyes along the z axis can frustrate accurate range-finding and autofocusing. By positioning the patient such that the head is supported and the neck muscles are permitted to release, z head position changes may be minimized.

In some embodiments, range-finding may involve determining a distance to a target tissue (e.g., the iris, retina, or trabecular meshwork). Topographical variations in the anterior target tissue surface may frustrate accurate range-finding and autofocusing. In the case of the iris, these variations result primarily from three elements: iris tilt, iris folds, and iris crypts. Iris tilt is a naturally occurring phenomenon. As a result, the iris plane will rarely reside perpendicular to the beam axis. The iris plane tilts about both the horizontal and vertical axes, and can tilt as much as 5°, which results in z variations of up to 700 μm from one edge of the iris to the other (assuming a roughly 11 mm horizontal iris diameter). An iris tilt system may be utilized to significantly reduce or eliminate this iris surface variation.

Iris folds are also a naturally occurring phenomenon. As the iris dilates, it folds like a drape, concentric to and away from the pupil. These folds can create significant z variations in the iris topography. To significantly reduce or eliminate iris folds, some methods may include introduction of a topical miotic solution, such as pilocarpine ophthalmic solution. In one embodiment, patents may be dosed with 1 or more drops of 2% pilocarpine ophthalmic solution at any or all of 60, 55, 50, 45, 40, 35, 30, 25, 20, 15, 10, or 5 minutes prior to the procedure to achieve high miosis, resistant to the potentially dilative effect of lasing the iris anterior to the iris dilator muscles during the procedure. Each patient may also be given 500 mg of acetaminophen (orally) 30 minutes prior to the procedure as a prophylaxis against headaches from ciliary body tension.

In the event of significant iridial surface topography post-miosis, the treatment beam focus may be shifted to first effectively treat one region of the target tissue, then successively shifted to effectively treat other regions of the target tissue until the full target tissue surface has received effective treatment. In some embodiments, the device may stack laser passes to expand this depth of focus and ensure that the entire anterior target tissue topography is treated within this depth of focus. As an illustrative example, the laser may treat the iris at four adjacent depths of focus, for a cumulative effective depth of focus of, for example, 1.6 mm. Once a laser pass over the treatment area is completed, then next laser pass may be performed until a total of four laser passes are performed. Laser passes are sequential but may be interrupted to accommodate fixation or patient comfort. Unless an operator terminates the treatment, the system may log interruptions and accommodate them on a subsequent laser pass at the same depth of focus. Therefore, if one or more interruption were to occur at each depth of focus, two laser passes may be completed at each of the four depths of focus, for a total of eight laser passes for that iris.

Iris crypts are another common phenomenon. They are created by spaces between the iris stromal fibers. In brown eyes, these crypts are typically filled with pigment and can therefore be ignored for purposes of the initial treatment sessions. Once the stromal pigment has been substantially eliminated outside of the crypts, stromal pigment might remain in the depths of the iris crypts. Pigment spots occur naturally in light eyes, so this remaining crypt pigment should not look unnatural and should barely be noticeable.

If remaining iris pigment spots bother the patient, the system can remove or reduce the remaining crypt pigment by slightly shifting the beam waist posteriorly into the stroma and rescanning the iris using this shifted waist position. This shifted waist setting may also be an option displayed for selection by the operator on the touchscreen interface. The distance of the shift of the beam waist may be equal to about 80% of the beam DOF to ensure delivery of high fluence within the pigmented crypts. If the crypt pigment remains 3-4 weeks after treatment with this posterior waist shift, this waist shift procedure may be repeated, posteriorly shifting the beam waist each time by another 80% of the DOF, until the crypt pigment is sufficiently eliminated.

The target tissue may be divided into multiple stages of treatment to remove different amounts or types of pigment at different times. Pigment, as previously discussed, may have varying physical properties that affect its responses to delivered laser power. Some pigment may require a higher laser power to raise its temperature such that it may be removed via macrophagic digestion. Thus, after a first treatment at a lower power, there may be some pigment that needs to be removed and require a higher laser power to do so. In this way, some methods of treatment may include determining, as part of the procedure, stages of delivery of laser power to the target tissue such that successive stages cause removal of less pigment but are delivered at a higher laser power. Thus, a given treatment session may include setting the laser system to the required laser power further based on a current stage of delivery and delivering the laser power based on the setting. A treatment session may include any number of stages of delivery, though typically, a treatment session includes only one stage of delivery as days or weeks may be needed for removal of the denatured pigment.

In some implementations, the system may deliver laser power over a number of steps to allow finer control of pigment denaturation. This may be a safety feature of the system to ensure that the lowest power is applied to the cells with the highest absorption coefficient to avoid ablation, that the highest power is applied to the cells with the lowest absorption coefficient to achieve efficacy, and that the intermediate powers are applied to the cells with the intermediate absorption coefficients to avoid ablation and achieve efficacy.

In some embodiments, procedures may rely on ablation of pigment or pigmented target tissue (e.g., pigment or tissue is eliminated by the laser application). In some embodiments, procedures may reply on the denaturation of the pigment or pigmented target tissue (e.g., the body's natura; immune response eliminates the denatured pigment or tissue over time). Some methods of the present disclosure may further include determining the proper amount of laser power to deliver based on a patient's immune response. Because macrophagic digestion is one method of removing pigment and activation of macrophages is an immune response, the removal of the pigment is proportional to the patient's immune response. Accordingly, some methods may include prescreening patients to determine the efficiency or aggressiveness of his or her macrophagic response to laser disruption of melanocytes, thereby further informing the MRE. The macrophagic response data could be entered into the system computer for calculation of any adjustments to the baseline fluence settings in isolation from or in combination with information derived from microbubble metrology.

Based on the immune response, the system may tailor the time interval between treatment stages to a particular person. This may include comparing the immune response level to a range of immune responses associated with a time interval between two of the stages. For example, two stages could be separated by 3-4 weeks based on a typical immune response (e.g., a 5 on a 1-10 scale, 10 being the highest immune response). The treatment procedure could have treatment intervals of 2-3 weeks for patients with an immune response rated between 8 and 10, and 5-6 weeks for patients with an immune response rated between 1 and 3. The method may then include, for example, reducing the time interval based on the comparison showing that the immune response level is higher than the range. The system may make a similar adjustment to the interval based on knowledge of a patient's inflammatory response. Examples of possible inflammatory response tests may include skin tests, where a patient is exposed to a substance expected to cause an allergic reaction. The data representative of the inflammatory response level quantifies the result of the skin test and may be used as described above. Similarly, in some embodiments, quantification of the immune response may be used to reduce or increase the laser power in any given treatment session and/or reduce or expand the time between treatments. For example, if the immune response shows that removal of pigment will occur 50% faster than a given baseline (e.g., for a typical immune response) then the time between sessions may be reduced by 50%.

In addition, inflammation is also an immune response to free melanin in the anterior chamber of the eye. Accordingly, prescreening patients to determine the aggressiveness of their immune responses to free melanin may be utilized by the system for adjustment or determination of the MRE, and the inflammatory response data may be utilized by the system for calculation of any adjustments to the baseline fluence settings. For macrophagic response to thermal disruption of stromal pigment, testing for the prevalence of cleaved caspase-1 p20 (a marker for inflammasome activation) and pro-inflammatory cytokines IL-1β and IL-6, both at baseline and perhaps in response to some perturbation to test reactivity may be used by the system. The system, in determining an inflammatory response to free melanin in the AC, may test or use results from tests for the prevalence of CD4+ T cells, angiogenin (AG), and pro-inflammatory cytokines (such as IL-1α, IL-1β, TNF-α, MMP-9. IL-2, IL-17), again, both at baseline and optionally in response to treatment.

Figure 5:
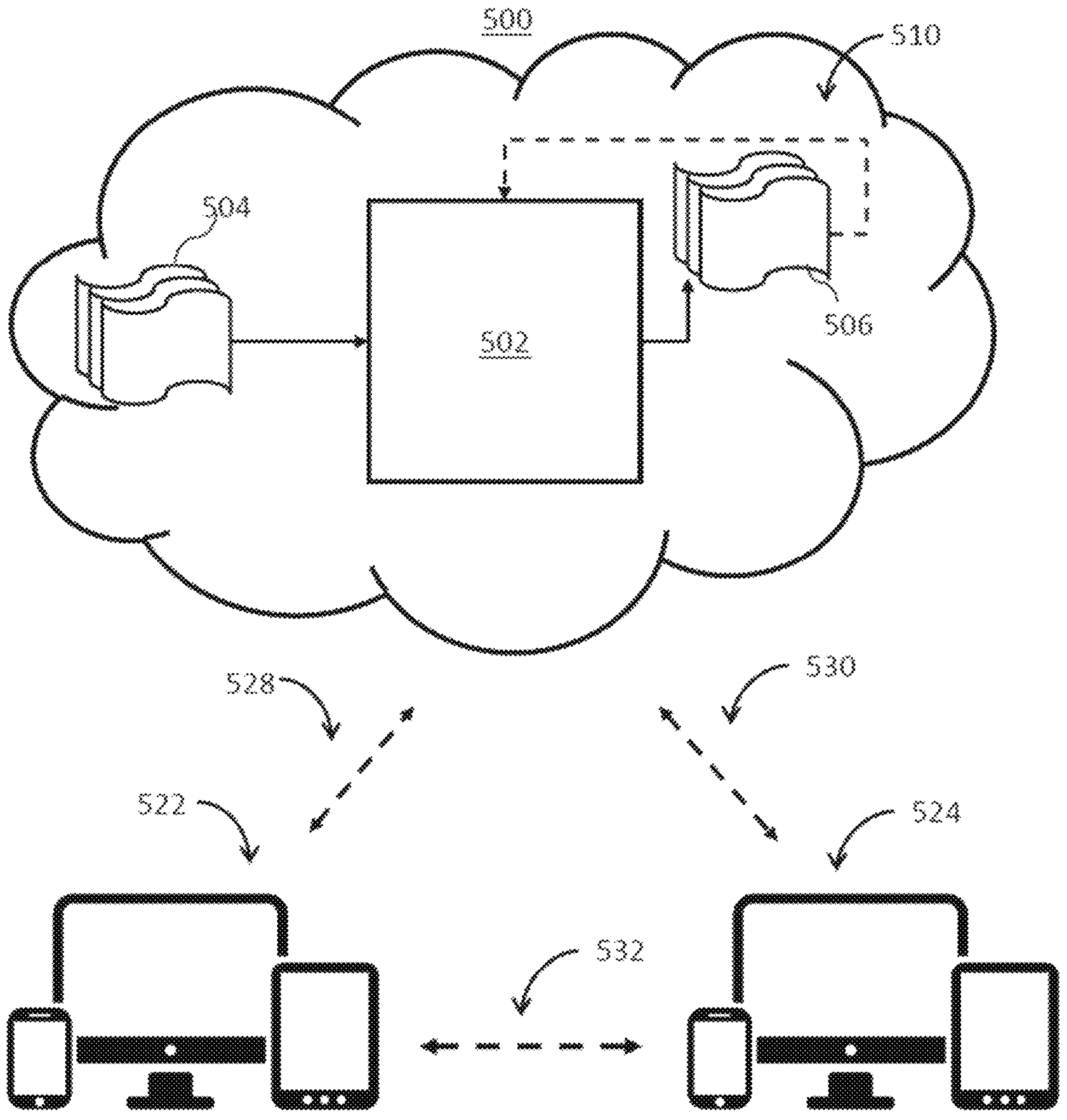
FIG. 5 shows an illustrative system for performing an eye-color changing procedure, in accordance with one or more embodiments.

FIG. 5 shows an illustrative system 500 for performing an eye-color changing procedure, in accordance with one or more embodiments. For example, system 500 may represent the components used for performing an eye-color changing procedure. For example, system 500 may power a local device to perform an eye-color changing procedure where the required determination (e.g., pattern to follow, laser power to deliver, identification of patient, etc.) are determined remotely and/or in the cloud. As shown in FIG. 5, system 500 may include user device 522 and user device 524. While shown as personal computers, in FIG. 5, it should be noted that user device 522 and user device 524 may be any computing device, including, but not limited to, a laptop computer, a tablet computer, a hand-held computer, other computer equipment (e.g., a server), including smart, wireless, wearable, and/or mobile devices. FIG. 5 also includes cloud components 510. Cloud components 510 may alternatively be any computing device as described above and may include any type of mobile terminal, fixed terminal, or other device. For example, cloud components 510 may be implemented as a cloud computing system and may feature one or more component devices. It should also be noted that system 500 is not limited to three devices. Users may, for instance, utilize one or more other devices to interact with one another, one or more servers, or other components of system 500. It should be noted that, while one or more operations are described herein as being performed by particular components of system 500, those operations may, in some embodiments, be performed by other components of system 500. As an example, while one or more operations are described herein as being performed by components of user device 522, those operations may, in some embodiments, be performed by components of cloud components 510. In some embodiments, the various computers and systems described herein may include one or more computing devices that are programmed to perform the described functions. Additionally, or alternatively, multiple users may interact with system 500 and/or one or more components of system 500. For example, in one embodiment, a first user and a second user (e.g., a technician and a physician) may interact with system 500 using two different components.

With respect to the components of user device 522, user device 524, and cloud components 510, each of these devices may receive content and data via input/output (e.g., I/O) paths. Each of these devices may also include processors and/or control circuitry to send and receive commands, requests, and other suitable data using the I/O paths. The control circuitry may comprise any suitable processing circuitry. Each of these devices may also include a user input interface and/or user output interface (e.g., a display) for use in receiving and displaying data. For example, as shown in FIG. 5, both user device 522 and user device 524 include a display upon which to display data (e.g., information related to an eye-color changing procedure).

In some embodiments, user device 522 and user device 524 may be touchscreen smartphones, and these displays also act as user input interfaces. It should be noted that in some embodiments, the devices may have neither user input interfaces nor displays and may instead receive and display content using another device (e.g., a dedicated display device such as a computer screen and/or a dedicated input device such as a remote control, mouse, voice input, etc.). Additionally, the devices in system 500 may run an application (or another suitable program). The application may cause the processors and/or control circuitry to perform operations related to an eye-color changing procedure.

Each of these devices may also include electronic storages. The electronic storages may include non-transitory storage media that electronically stores information. The electronic storage media of the electronic storages may include one or both of (i) system storage that is provided integrally (e.g., substantially non-removable) with servers or client devices or (ii) removable storage that is removably connectable to the servers or client devices via, for example, a port (e.g., a USB port, a firewire port, etc.) or a drive (e.g., a disk drive, etc.). The electronic storages may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. The electronic storages may include one or more virtual storage resources (e.g., cloud storage, a virtual private network, and/or other virtual storage resources). The electronic storages may store software algorithms, information determined by the processors, information obtained from servers, information obtained from client devices, or other information that enables the functionality as described herein.

FIG. 5 also includes communication paths 528, 530, and 532. Communication paths 528, 530, and 532 may include the Internet, a mobile phone network, a mobile voice or data network (e.g., a 5G or LTE network), a cable network, a public switched telephone network, or other types of communications network or combinations of communications networks. Communication paths 528, 530, and 532 may separately or together include one or more communications paths, such as a satellite path, a fiber-optic path, a cable path, a path that supports Internet communications (e.g., IPTV), free-space connections (e.g., for broadcast or other wireless signals), or any other suitable wired or wireless communications path or combination of such paths. The computing devices may include additional communication paths linking a plurality of hardware, software, and/or firmware components operating together. For example, the computing devices may be implemented by a cloud of computing platforms operating together as the computing devices.

Cloud components 510 may be a database configured to store user data for a user. For example, the database may include user data that the system has collected about the user through prior operations and/or procedures. Alternatively, or additionally, the system may act as a clearing house for multiple sources of information about the user. Cloud components 510 may also include control circuitry configured to perform the various operations needed to perform an eye-color changing procedure.

Cloud components 510 include machine learning model 502. Machine learning model 502 may take inputs 504 and provide outputs 506. The inputs may include multiple data sets such as a training data set and a test data set. Each of the plurality of data sets (e.g., inputs 504) may include data subsets related to user data, an eye-color changing procedure, patient progress, and/or results. In some embodiments, outputs 506 may be fed back to machine learning model 502 as input to train machine learning model 502 (e.g., alone or in conjunction with user indications of the accuracy of outputs 506, labels associated with the inputs, or with other reference feedback information). In another embodiment, machine learning model 502 may update its configurations (e.g., weights, biases, or other parameters) based on the assessment of its prediction (e.g., outputs 506) and reference feedback information (e.g., indication of accuracy, results of procedure, reference labels, and/or other information). In another embodiment, where machine learning model 502 is a neural network, connection weights may be adjusted to reconcile differences between the neural network's prediction and the reference feedback. In a further use case, one or more neurons (or nodes) of the neural network may require that their respective errors be sent backward through the neural network to facilitate the update process (e.g., backpropagation of error). Updates to the connection weights may, for example, be reflective of the magnitude of error propagated backward after a forward pass has been completed. In this way, for example, the machine learning model 502 may be trained to generate better predictions (e.g., predictions related to an appropriate pattern to follow, laser power, level of eye-color change, number of procedures, length of procedures, etc.)

In some embodiments, machine learning model 502 may include an artificial neural network. In some embodiments, machine learning model 502 may include a large language model. In such embodiments, machine learning model 502 may include an input layer and one or more hidden layers. Each neural unit of machine learning model 502 may be connected with many other neural units of machine learning model 502. Such connections may be enforcing or inhibitory in their effect on the activation state of connected neural units. In some embodiments, each individual neural unit may have a summation function that combines the values of all of its inputs together. In some embodiments, each connection (or the neural unit itself) may have a threshold function such that the signal must surpass before it propagates to other neural units. Machine learning model 502 may be self-learning and trained, rather than explicitly programmed, and may perform significantly better in certain areas of problem solving, as compared to traditional computer programs. During training, an output layer of machine learning model 502 may correspond to a classification of machine learning model 502 and an input known to correspond to that classification may be input into an input layer of machine learning model 502 during training. During testing, an input without a known classification may be input into the input layer, and a determined classification may be output.

In some embodiments, machine learning model 502 may include multiple layers (e.g., where a signal path traverses from front layers to back layers). In some embodiments, backpropagation techniques may be utilized by machine learning model 502 where forward stimulation is used to reset weights on the front neural units. In some embodiments, stimulation and inhibition for machine learning model 502 may be more free flowing, with connections interacting in a more chaotic and complex fashion. During testing, an output layer of machine learning model 502 may indicate whether or not a given input corresponds to a classification of machine learning model 502 (e.g., an eye-color change requested, a pattern to follow, a laser power to deliver, etc.).

Figure 6:
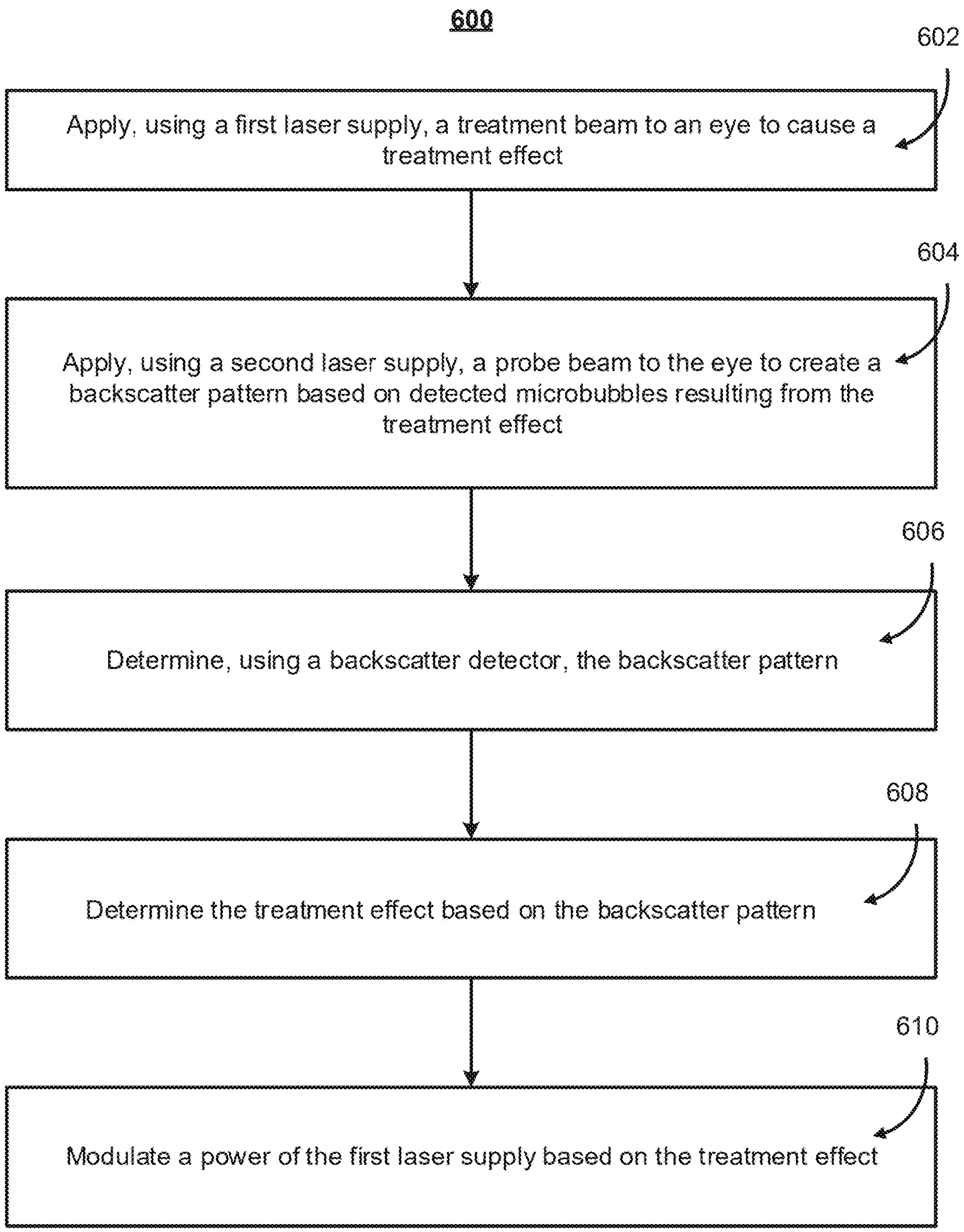
FIG. 6 shows steps for detecting microbubbles, in accordance with one or more embodiments.

FIG. 6 shows steps for determining how much power to apply to an eye to change the color without damaging the eye. For example, process 600 may represent the steps taken by one or more devices as shown in FIGS. 1-5 when performing an eye-color changing procedure.

At step 602, process 600 (e.g., via one or more components of FIGS. 1-5) may apply, using a first laser supply, a treatment beam to an eye to cause a treatment effect. For example, the treatment effect may be a microbubble formation. In some embodiments, the system may determine a power output of the first laser supply before emitting the treatment beam. The system may need a high enough power output to change the eye color but a low enough power output such that the laser does not damage the eye. In some embodiments, the system may select an initial power output of the first laser supply and may increase the power output until reaching the proper power output. For example, the system may determine the proper power output based on detecting microbubbles in the eye. In some embodiments, the system may apply the treatment beam to the eye using first power supply 202, as shown in FIG. 2A.

At step 604, process 600 (e.g., via one or more components of FIGS. 1-5) may apply, using a second laser supply, a probe beam to the eye to create a backscatter pattern based on detected microbubbles resulting from the treatment effect. Applying the probe beam to the eye may create a backscatter pattern based on the microbubbles resulting from the treatment effect. In some embodiments, the system may apply the probe beam to the eye using second power supply 204, as shown in FIG. 2A. In some embodiments, step 604 may occur simultaneously with step 602 or step 604 may overlap with step 602.

At step 606, process 600 (e.g., via one or more components of FIGS. 1-5) may determine, using a backscatter detector, the backscatter pattern. For example, the backscatter pattern may be a change indicating that a treatment effect is occurring. For example, the backscatter pattern may be a threshold pattern change indicating that the treatment effect (e.g., microbubble formation) is occurring. In some embodiments, the backscatter pattern includes a profile value of the beam profile of the backscattered probe beam. After microbubbles form, the profile value may indicate that the treatment effect is occurring. In some embodiments, the profile value may be a variation in backscatter power detected over time following the application of the treatment beam. In some embodiments, the system may determine the backscatter pattern using backscatter detector 226, as shown in FIG. 2A.

At step 608, process 600 (e.g., via one or more components of FIGS. 1-5) may determine the treatment effect based on the backscatter pattern. For example, the system may identify a threshold pattern change, profile value, or other backscatter pattern. This may indicate that the treatment effect (e.g., microbubble formation) has occurred. In some embodiments, the system may determine the treatment effect using element 340, as shown in FIG. 3.

At step 610, process 600 (e.g., via one or more components of FIGS. 1-5) may modulate a power of the first laser supply based on the treatment effect. For example, the system may set the power level of the treatment beam based on the level at which the treatment effect occurs. In some embodiments, the system may set the power level of the treatment beam to be equal to the level at which the treatment effect occurs. In some embodiments, the system may set the power level of the treatment beam to be slightly less than the level at which the treatment effect occurs. In some embodiments, the system may set the power level of the treatment beam to another level. In some embodiments, the system may modulate the power of the first laser supply using power modulator 418, as shown in FIGS. 4A and 4B.

The above-described embodiments of the present disclosure are presented for purposes of illustration and not of limitation. Furthermore, it should be noted that the features and limitations described in any one embodiment may be applied to any other embodiment herein, and flowcharts or examples relating to one embodiment may be combined with any other embodiment in a suitable manner, done in different orders, or done in parallel. In addition, the systems and methods described herein may be performed in real time. It should also be noted that the systems and/or methods described above may be applied to, or used in accordance with, other systems and/or methods.

The present techniques will be better understood with reference to the following enumerated embodiments:

1. A method comprising a first laser supply, wherein the first laser supply emits a treatment beam applied to a first region of a target tissue of an eye, and wherein the treatment beam creates a treatment effect, a second laser supply, wherein the second laser supply emits a probe beam applied to a second region of the eye, and wherein the probe beam creates a backscatter pattern based on detected microbubbles, a backscatter detector, wherein the backscatter detector detects the backscatter pattern, a processor, wherein the processor is configured to determine the treatment effect based on the backscatter pattern, and a power modulator, wherein the power modulator is configured to modulate a power level of the first laser supply based on the treatment effect determined by the processor.
2. A method comprising applying, using a first laser supply, a treatment beam to a target tissue of an eye to cause a treatment effect, applying, using a second laser supply, a probe beam to the eye to create a backscatter pattern based on detected microbubbles resulting from the treatment effect, determining, using a backscatter detector, the backscatter pattern, determining the treatment effect based on the backscatter pattern, and modulating a power of the first laser supply based on the treatment effect.
3. A method comprising determining a first setting for a treatment beam, applying a treatment beam to a target tissue of an eye to cause a treatment effect, applying a probe beam to the eye to create a backscatter pattern based on detected microbubbles resulting from the treatment effect, determining the treatment effect based on the backscatter pattern, modulating a power of the treatment beam based on the treatment effect, and determining a second setting for the treatment beam based on the treatment effect.
4. The method of any one of the preceding embodiments, wherein a gain medium of the first laser supply comprises Nd:YAG.
5. The method of any one of the preceding embodiments, wherein a gain medium of the first laser supply comprises semiconductor materials layered to form a diode.
6. The method of any one of the preceding embodiments, wherein a gain medium of the first laser supply comprises argon gas.
7. The method of any one of the preceding embodiments, wherein a power output of the first laser supply is determined before the treatment beam is emitted.
8. The method of any one of the preceding embodiments, further comprising increasing a power output of the first laser supply while applying the treatment beam using the first laser supply, and scanning the treatment beam in a pre-determined pattern about a first region of the eye.
9. The method of any one of the preceding embodiments, wherein the first region of the eye comprises an iris of the eye.
10. The method of any one of the preceding embodiments, wherein the first region of the eye comprises a trabecular meshwork of the eye.
11. The method of any one of the preceding embodiments, wherein the first region of the eye comprises a retina of the eye.
12. The method of any one of the preceding embodiments, wherein the first region of the eye comprises an iris pigment epithelium (IPE).
13. The method of any one of the preceding embodiments, wherein a wavelength of the treatment beam comprises infrared radiation.
14. The method of any one of the preceding embodiments, wherein a wavelength of the treatment beam comprises a visible light.

15. The method of any one of the preceding embodiments, wherein a gain medium of the second laser supply comprises semiconductor materials layered to form a diode.
16. The method of any one of the preceding embodiments, further comprising determining a power output of the second laser supply before applying the treatment beam.
17. The method of any one of the preceding embodiments, further comprising increasing a power output of the second laser supply while applying the probe beam using the second laser supply, and scanning the probe beam in a pre-determined pattern about a second region of the eye.
18. The method of any one of the preceding embodiments, wherein the second region of the eye comprises a first region of the eye, the first region of the eye being scanned in the pre-determined pattern by the treatment beam.
19. The method of any one of the preceding embodiments, wherein a wavelength of the probe beam comprises infrared radiation.
20. The method of any one of the preceding embodiments, wherein a wavelength of the probe beam comprises a green light.
21. The method of any one of the preceding embodiments, wherein an incidence angle of the probe beam relative to the treatment beam is less than or equal to 75°.
22. The method of any one of the preceding embodiments, wherein the backscatter detector comprises an optical sensor, and wherein the optical sensor comprises an optical filter that passes the probe beam and limits passage of other light.
23. The method of any one of the preceding embodiments, wherein the backscatter pattern is based on a size of one or more microbubbles.
24. The method of any one of the preceding embodiments, wherein the backscatter pattern is based on a density of one or more groups of microbubbles.
25. The method of any one of the preceding embodiments, wherein the backscatter pattern is based on a duration associated with one or more microbubbles.
26. The method of any one of the preceding embodiments, further comprising modulating the power using a Pockels cell.
27. The method of any one of the preceding embodiments, further comprising modulating the power using an acousto-optic modulator.
28. The method of any one of the preceding embodiments, further comprising modulating the power using an electro-optic modulator.
29. The method of any one of the preceding embodiments, further comprising modulating the power using a semiconductor gain medium.
30. The method of any one of the preceding embodiments, wherein the treatment effect comprises a denaturation of at least one of melanosomes or melanocytes.
31. The method of any one of the preceding embodiments, wherein the treatment effect comprises rupturing at least one of melanosomes or melanocytes.
32. The method of any one of the preceding embodiments, wherein the treatment effect comprises aesthetic iris iridoplasty.
33. The method of any one of the preceding embodiments, wherein the treatment effect comprises therapeutic iris iridoplasty.
34. The method of any one of the preceding embodiments, wherein the treatment effect comprises a mitigating effect of retinitis pigmentosa.
35. The method of any one of the preceding embodiments, wherein the treatment effect comprises a microbubble formation.
36. The method of any one of the preceding embodiments, wherein the treatment effect comprises a minimum radiative exposure value capable of denaturing pigment granules.
37. The method of any one of the preceding embodiments, wherein the treatment effect comprises a minimum radiative exposure value capable of ablating pigment granules.
38. The method of any one of the preceding embodiments, further comprising determining a first setting for the treatment beam, and determining a second setting for the treatment beam based on the treatment effect.
39. The method of any one of the preceding embodiments, further comprising distinguishing the first setting and the second setting based on treatment beam characteristics, wherein the treatment beam characteristics comprise one or more of a wavelength, a color, a collimated beam, a beam angle, a beam diameter, beam dimensions, and a contribution of the treatment beam to the backscatter pattern.
40. The method of any one of the preceding embodiments, wherein the treatment beam does not contribute to the backscatter pattern.
41. The method of any one of the preceding embodiments, wherein the backscatter pattern is a threshold pattern change indicating that the treatment effect is occurring.
42. The method of any one of the preceding embodiments, wherein the backscatter pattern is a profile value indicating that the treatment effect is occurring.
43. One or more non-transitory, computer-readable media storing computer-executable instructions that, when executed by one or more data processing apparatuses, cause operations comprising those of any of embodiments 1-42.
44. A system comprising one or more processors and memory storing instructions that, when executed by the processors, cause the processors to effectuate operations comprising those of any of embodiments 1-42.
45. A system comprising means for performing any of embodiments 1-42.
46. A system comprising cloud-based circuitry for performing any of embodiments 1-42.

What is claimed is:

1. A dual-beam laser treatment device for determining treatment effects based on backscatter detection, the dual-beam laser treatment device comprising:
- a first laser supply, wherein the first laser supply emits a treatment beam applied to a first region of an eye, and wherein the treatment beam creates a treatment effect;
- a second laser supply, wherein the second laser supply emits a probe beam applied in a pre-determined pattern to a second region of the eye, and wherein the probe beam creates a backscatter pattern based on detected microbubbles;
- a backscatter detector, wherein the backscatter detector detects the backscatter pattern;
- a processor, wherein the processor is configured to;
  - while the probe beam is applied, increase a power output of the second laser supply; and
  - determine the treatment effect based on the backscatter pattern; and a power modulator, wherein the power modulator is configured to modulate a power level of the first laser supply based on the treatment effect determined by the processor.

2. A method for determining treatment effects on eyes based on backscatter detection, the method comprising:

applying, using a first laser supply, a treatment beam to an eye to cause a treatment effect;

applying, using a second laser supply, a probe beam in a pre-determined pattern about a region of the eye to create a backscatter pattern based on detected microbubbles resulting from the treatment effect;

while applying the probe beam using the second laser supply, increasing a power output of the second laser supply;

determining, using a backscatter detector, the backscatter pattern;

determining the treatment effect based on the backscatter pattern; and modulating a power of the first laser supply based on the treatment effect.

3. The method of claim 2, wherein a gain medium of the first laser supply comprises Nd:YAG.

4. The method of claim 2, wherein a gain medium of the first laser supply comprises semiconductor materials layered to form a diode.

5. The method of claim 2, wherein a gain medium of the first laser supply comprises argon gas.

6. The method of claim 2, wherein a power output of the first laser supply is determined before the treatment beam is emitted.

7. The method of claim 2, further comprising:

increasing a power output of the first laser supply while applying the treatment beam using the first laser supply; and scanning the treatment beam in a pre-determined pattern about an additional region of the eye.

8. The method of claim 7, wherein the additional region of the eye comprises an iris of the eye.

9. The method of claim 7, wherein the additional region of the eye comprises a trabecular meshwork of the eye.

10. The method of claim 7, wherein the additional region of the eye comprises a retina of the eye.

11. The method of claim 7, wherein the additional region of the eye comprises an iris pigment epithelium (IPE).

12. The method of claim 2, wherein a wavelength of the treatment beam comprises infrared radiation.

13. The method of claim 2, wherein a wavelength of the treatment beam comprises a visible light.

14. The method of claim 2, wherein a gain medium of the second laser supply comprises semiconductor materials layered to form a diode.

15. The method of claim 2, further comprising determining the power output of the second laser supply before applying the treatment beam.

16. The method of claim 2, wherein the region of the eye comprises an additional region of the eye, the additional region of the eye being scanned in the pre-determined pattern by the treatment beam.

17. The method of claim 2, wherein a wavelength of the probe beam comprises infrared radiation.

18. The method of claim 2, wherein a wavelength of the probe beam comprises a green light.

19. The method of claim 2, wherein an incidence angle of the probe beam relative to the treatment beam is less than or equal to 75°.

20. The method of claim 2, wherein the backscatter detector comprises an optical sensor, and wherein the optical sensor comprises an optical filter that passes the probe beam and limits passage of other light.

21. The method of claim 2, wherein the backscatter pattern is based on a size of one or more microbubbles.

22. The method of claim 2, wherein the backscatter pattern is based on a density of one or more groups of microbubbles.

23. The method of claim 2, wherein the backscatter pattern is based on a duration associated with one or more microbubbles.

24. The method of claim 2, further comprising modulating the power of the first laser supply using a Pockels cell.

25. The method of claim 2, further comprising modulating the power of the first laser supply using an acousto-optic modulator.

26. The method of claim 2, further comprising modulating the power of the first laser supply using an electro-optic modulator.

27. The method of claim 2, further comprising modulating the power of the first laser supply using a semiconductor gain medium.

28. The method of claim 2, wherein the treatment effect comprises a denaturation of at least one of melanosomes or melanocytes.

29. The method of claim 2, wherein the treatment effect comprises rupturing at least one of melanosomes or melanocytes.

30. The method of claim 2, wherein the treatment effect comprises aesthetic iris iridoplasty.

31. The method of claim 2, wherein the treatment effect comprises therapeutic iris iridoplasty.

32. The method of claim 2, wherein the treatment effect comprises a mitigating effect of retinitis pigmentosa.

33. The method of claim 2, wherein the treatment effect comprises a microbubble formation.

34. The method of claim 2, wherein the treatment effect comprises a minimum radiative exposure value capable of denaturing pigment granules.

35. The method of claim 2, wherein the treatment effect comprises a minimum radiative exposure value capable of ablating pigment granules.

36. The method of claim 2, further comprising:

determining a first setting for the treatment beam; and determining a second setting for the treatment beam based on the treatment effect.

37. The method of claim 36, further comprising:

distinguishing the first setting and the second setting based on treatment beam characteristics, wherein the treatment beam characteristics comprise one or more of a wavelength, a color, a collimated beam, a beam angle, a beam diameter, beam dimensions, and a contribution of the treatment beam to the backscatter pattern.

38. The method of claim 2, wherein the backscatter pattern is a threshold pattern change indicating that the treatment effect is occurring.

39. The method of claim 2, wherein the backscatter pattern is a profile value indicating that the treatment effect is occurring.

40. One or more non-transitory, computer-readable media comprising instructions that, when executed by one or more processors, cause operations comprising:

determining a first setting for a treatment beam;

applying, using a first laser supply, a treatment beam to an eye to cause a treatment effect;

applying, using a second laser supply, a probe beam in a pre-determined pattern about a region of the eye to create a backscatter pattern based on detected microbubbles resulting from the treatment effect;

while applying the probe beam using the second laser supply, increasing a power output of the second laser supply;

determining the treatment effect based on the backscatter pattern;

modulating a power of the treatment beam based on the treatment effect; and determining a second setting for the treatment beam based on the treatment effect.

41. The one or more non-transitory, computer-readable media of claim 40, wherein a wavelength of the treatment beam comprises a visible light.

42. The one or more non-transitory, computer-readable media of claim 40, wherein the backscatter pattern is based on a size of one or more microbubbles.

* * * * *